US010323243B2

(12) United States Patent
Ellington et al.

(10) Patent No.: US 10,323,243 B2
(45) Date of Patent: Jun. 18, 2019

(54) THERMOSTABLE REVERSE TRANSCRIPTASE

(71) Applicant: BOARD OF REGENTS, THE UNIVERSITY OF TEXAS SYSTEM, Austin, TX (US)

(72) Inventors: Andrew Ellington, Austin, TX (US); Jared Ellefson, Austin, TX (US); Jimmy Gollihar, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 7 days.

(21) Appl. No.: 15/410,211

(22) Filed: Jan. 19, 2017

(65) Prior Publication Data

US 2017/0327818 A1    Nov. 16, 2017

Related U.S. Application Data

(60) Provisional application No. 62/280,451, filed on Jan. 19, 2016.

(51) Int. Cl.
*C12N 9/12* (2006.01)
*C12N 15/10* (2006.01)
*G01N 27/447* (2006.01)

(52) U.S. Cl.
CPC ....... *C12N 15/1096* (2013.01); *C12N 9/1276* (2013.01); *G01N 27/447* (2013.01)

(58) Field of Classification Search
CPC combination set(s) only.
See application file for complete search history.

(56) References Cited

U.S. PATENT DOCUMENTS

| 8,435,775 | B2* | 5/2013 | Holliger | C12N 9/1252 435/183 |
| 9,169,471 | B2* | 10/2015 | Holliger | C12N 9/1241 |
| 9,938,511 | B2* | 4/2018 | Holliger | C12N 9/1241 |
| 2002/0076768 | A1 | 6/2002 | Kuroita et al. | |
| 2003/0134292 | A1 | 7/2003 | Farchaus | |
| 2003/0228616 | A1 | 12/2003 | Arezi et al. | |
| 2004/0005594 | A1 | 1/2004 | Holliger et al. | |
| 2004/0005599 | A1 | 1/2004 | Schoenbrunner et al. | |
| 2004/0009486 | A1 | 1/2004 | Sorge et al. | |
| 2005/0069887 | A1 | 3/2005 | Kitabayashi et al. | |
| 2007/0020653 | A1 | 1/2007 | Holliger et al. | |
| 2007/0134682 | A1 | 6/2007 | Holliger et al. | |
| 2009/0305345 | A1 | 12/2009 | Holliger et al. | |
| 2010/0035767 | A1 | 2/2010 | Holliger et al. | |
| 2011/0301041 | A1* | 12/2011 | Davidson | C12N 9/1252 506/2 |

FOREIGN PATENT DOCUMENTS

| WO | WO 2002/022869 | 3/2002 |
| WO | WO 2005/045015 | 5/2005 |
| WO | WO 2005/045072 | 5/2005 |
| WO | WO 2008/029085 | 3/2008 |
| WO | WO 2008/050104 | 5/2008 |

OTHER PUBLICATIONS

Ellefson et al., "Synthetic evolutionary origin of a proofreading revers transcriptase", Science, 352: 1590-1593, 2016.
Ellefson et al., "Synthetic evolutionary origin of a proofreading revers transcriptase", Science, 352: 1590-1593, 2016. Supplementary Materials.
International Search Report and Written Opinion issued in International Application No. PCT/US17/14082, dated Jun. 8, 2017.
Nishioka et al., "Long and accurate PCR with a mixture of KOD DNA polymerase and its exonuclease deficient mutant enzyme", Journal of Biotechnology, 88: 141-149, 2001.

* cited by examiner

*Primary Examiner* — Kagnew H Gebreyesus
(74) *Attorney, Agent, or Firm* — Parker Highlander PLLC

(57) ABSTRACT

Embodiments of the disclosure concern methods and compositions related to generation and/or use of proofreading reverse transcriptases, including those that are thermophilic or hyperthermophilic. The disclosure encompasses specific recombinant polymerases and their use. In some embodiments, the polymerases are utilized for RNA sequencing in the absence of generation of a cDNA intermediate.

20 Claims, 15 Drawing Sheets

Specification includes a Sequence Listing.

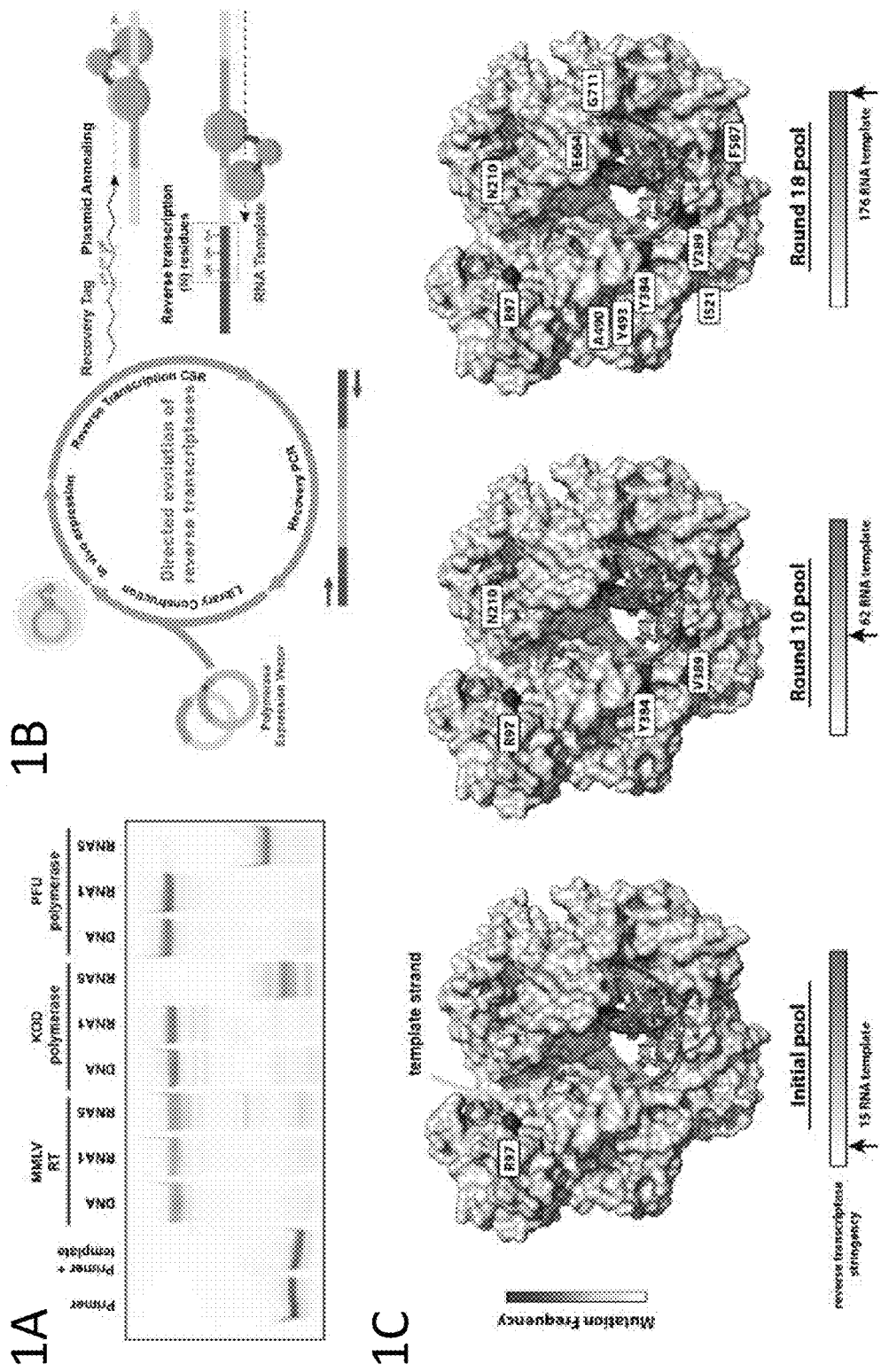
FIGS. 1A, 1B, and 1C

FIGS. 5A, 5B, and 5C

SEQUENCE LISTING

<160> NUMBER OF SEQ ID NOS: 11

<210> SEQ ID NO 1
<211> LENGTH: 774
<212> TYPE: PRT
<213> ORGANISM: Pyrococcus kodakaraensis

<400> SEQUENCE: 1

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
```

```
                405                 410                 415
Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 2
<211> LENGTH: 774
<212> TYPE: PRT
<213> ORGANISM: Artificial Sequence
<220> FEATURE:
<223> OTHER INFORMATION: Synthetic Peptide
```

<400> SEQUENCE: 2

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Leu Tyr Ala Leu Leu Lys Asp Asp Ser Ala Ile
        35                  40                  45

Glu Glu Val Lys Lys Ile Thr Ala Glu Arg His Ser Thr Val Val Thr
    50                  55                  60

Val Lys Arg Val Glu Lys Val Gln Lys Phe Leu Gly Arg Ser Val
65                  70                  75                  80

Glu Val Trp Lys Leu Tyr Phe Thr His Pro Gln Asp Val Pro Ala Ile
            85                  90                  95

Met Asp Lys Ile Arg Glu His Pro Ala Val Ile Asp Ile Tyr Glu Tyr
            100                 105                 110

Asp Ile Pro Phe Ala Ile Arg Tyr Leu Ile Asp Lys Gly Leu Val Pro
        115                 120                 125

Met Glu Gly Asp Glu Glu Leu Lys Leu Leu Ala Leu Asp Ile Gly Thr
    130                 135                 140

Pro Cys His Glu Gly Glu Val Phe Ala Glu Gly Pro Ile Leu Met Ile
145                 150                 155                 160

Ser Tyr Ala Asp Glu Gly Thr Arg Val Ile Thr Trp Arg Asn Val
            165                 170                 175

Asp Leu Pro Tyr Val Asp Val Leu Ser Thr Glu Arg Glu Met Ile Gln
        180                 185                 190

Arg Phe Leu Arg Val Val Lys Glu Lys Asp Pro Asp Val Leu Ile Thr
    195                 200                 205

Tyr Asn Gly Asp Asn Phe Asp Phe Ala Tyr Leu Lys Lys Arg Cys Glu
210                 215                 220

Lys Leu Gly Ile Asn Phe Thr Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Val Asn Leu Pro Ile
        260                 265                 270

Tyr Thr Leu Glu Ala Val Tyr Glu Ala Val Phe Gly Gln Pro Lys Glu
    275                 280                 285

Lys Val Tyr Ala Glu Glu Ile Thr Thr Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Lys Glu Phe Met Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg His Gln Ser His
370                 375                 380

Glu Gly Gly Tyr Ile Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415
```

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Arg Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Leu Tyr Gly Tyr
                485                 490                 495

Tyr Gly Tyr Ala Arg Ala Arg Trp Tyr Cys Lys Glu Cys Ala Glu Ser
            500                 505                 510

Val Ile Ala Trp Gly Arg Glu Tyr Ile Thr Met Thr Ile Lys Glu Ile
        515                 520                 525

Glu Glu Lys Tyr Gly Phe Lys Leu Ile Tyr Ser Asp Thr Asp Gly Phe
    530                 535                 540

Phe Ala Thr Ile Pro Gly Ala Glu Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Leu Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Lys Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Val Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Tyr Gly Tyr Arg Lys
            740                 745                 750

Glu Asp Leu Trp Tyr Gln Lys Thr Arg Gln Val Gly Leu Ser Ala Arg
        755                 760                 765

Leu Lys Pro Lys Gly Thr
    770

<210> SEQ ID NO 3
<211> LENGTH: 774
<212> TYPE: PRT
<213> ORGANISM: Artificial Sequence
<220> FEATURE:
<223> OTHER INFORMATION: Synthetic Peptide

<400> SEQUENCE: 3

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Leu Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Met Asp Lys Ile Arg Glu His Pro Ala Val Ile Asp Ile Tyr Glu Tyr
                100                 105                 110

Asp Ile Pro Phe Ala Ile Arg Tyr Leu Ile Asp Lys Gly Leu Val Pro
            115                 120                 125

Met Glu Gly Asp Glu Glu Leu Lys Leu Leu Ala Phe Asp Ile Glu Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
                180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg His Gln Ser His
        370                 375                 380

Glu Gly Gly Tyr Ile Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415
```

-continued

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Arg Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Leu Tyr Gly Tyr
                485                 490                 495

Tyr Gly Tyr Ala Arg Ala Arg Trp Tyr Cys Lys Glu Cys Ala Glu Ser
            500                 505                 510

Val Ile Ala Trp Gly Arg Glu Tyr Leu Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Leu Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Lys Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Val Asp Arg Ala Ile Pro Phe Asp Glu Phe
705                 710                 715                 720

Asp Pro Thr Lys His Lys Tyr Asp Ala Glu Tyr Tyr Ile Glu Lys Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Arg
        755                 760                 765

Leu Lys Pro Lys Gly Thr
    770

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

```
Met Leu Ala Phe Asp Ile Glu Thr Leu Tyr His Glu Gly Glu Glu Phe
1               5                   10                  15
```

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 5

```
Leu Leu Ala Leu Asp Ile Gly Thr Pro Cys His Glu Gly Glu Val Phe
1               5                   10                  15
```

<210> SEQ ID NO 6
<211> LENGTH: 45
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (25)..(25)
<223> OTHER INFORMATION: Hydroxylated Alanine

<400> SEQUENCE: 6
ccctcgcagc cgtccaacca actcagatcg atcgatcgat cgatc                45

<210> SEQ ID NO 7
<211> LENGTH: 45
<212> TYPE: RNA
<213> ORGANISM: Artificial Sequence
<220> FEATURE:
<223> OTHER INFORMATION: Synthetic Fragment

<400> SEQUENCE: 7
gggagcgucg gcagguuggu ugagucuagc uagcuagcua gcuag                45

<210> SEQ ID NO 8
<211> LENGTH: 25
<212> TYPE: DNA
<213> ORGANISM: Artificial Sequence
<220> FEATURE:
<223> OTHER INFORMATION: Synthetic Primer

<400> SEQUENCE: 8
ccctcgcagc cgtccaacca actca                      25

<210> SEQ ID NO 9
<211> LENGTH: 36
<212> TYPE: DNA
<213> ORGANISM: Artificial Sequence
<220> FEATURE:
<223> OTHER INFORMATION: Synthetic Primer

<400> SEQUENCE: 9
gggagcgtcg gcaggttggt tgagtgcctc ttgttt          36

<210> SEQ ID NO 10
<211> LENGTH: 50
<212> TYPE: DNA
<213> ORGANISM: Artificial sequence
<220> FEATURE:
<223> OTHER INFORMATION: Synthetic primer

<400> SEQUENCE: 10
acgcaaggag gcaaacggaa acaacgagc aggagggacg gcagcgaggg              50

```
<210> SEQ ID NO 11
<211> LENGTH: 21
<212> TYPE: DNA
<213> ORGANISM: Artificial sequence
<220> FEATURE:
<223> OTHER INFORMATION: Synthetic primer

<400> SEQUENCE: 11
ccctcgctgc cgtccctcct g                                              21
```

THERMOSTABLE REVERSE TRANSCRIPTASE

This application claims the benefit of U.S. Provisional Patent Application No. 62/280,451, filed Jan. 19, 2016, the entirety of which is incorporated herein by reference.

STATEMENT REGARDING FEDERALLY SPONSORED RESEARCH OR DEVELOPMENT

This invention was made with government support under Grant no. FA9550-10-1-0169 awarded by the Air Force Office of Scientific Research and Grant no. HR0011-12-2-0001 awarded by Defense Advanced Research Projects Agency. The government has certain rights in the invention.

TECHNICAL FIELD

Embodiments of the disclosure encompass at least the fields of molecular biology, cell biology, biochemistry, research, medicine, and diagnostics.

BACKGROUND

Temin and Baltimore's discovery of reverse transcriptase (RT) altered the understanding of molecular biology (Temin and Mizutani, 1970; Baltimore, 1970). It demonstrated that genetic information does not flow unidirectionally, from DNA to RNA to proteins, but could also flow in the reverse direction from RNA back to DNA. RT enzymes were initially found in retroviruses (e.g., Moloney murine leukemia virus (MMLV)) but have since been discovered in other RNA elements (e.g., group II introns, transposable elements) (Boeke and Stoye, 1997) and are primarily responsible for converting an RNA genome into DNA for integration into a host's chromosome. Since its discovery, RT has revolutionized the understanding of eukaryotic biology enabling the conversion of mature mRNA into cDNA, without the introns present in genomic DNA. Since these foundational studies, the RT has become a ubiquitous tool in molecular biology driving enabling technologies like next-generation RNA-Sequencing.

All known RTs are derived from a shared common ancestor (Xiong and Eickbush, 1990). These enzymes are characteristically mesophilic and lack a proofreading domain (3'-5' exonuclease), which is thought to be the cause of their high error rate in vitro (Roberts et al., 1988). As a result of this, insertion of the correct nucleotide is driven entirely by Watson-Crick hydrogen bonding and geometry (Kim et al., 2005). In addition, the low polymerization temperature has been a notorious issue inhibiting efficient reverse transcription due to RNAs adopting stable secondary structures at lower temperatures (Klarmann et al., 1993). In contrast to RTs, high fidelity DNA polymerases have emerged and innovated biotechnology-enabling unprecedented fidelity and high thermostability.

Monomeric archaeal Family-B polymerases (polB) have been widely adopted in modern molecular biology due to their hyperthermostability, processivity, and fidelity. These enzymes have clear advantages over RTs but they have little to no activity on RNA templates. A comparison between two common archaeal enzymes (KOD and PFU) (Takagi et al., 1997; Lundberg et al., 1991) and MMLV RT reveals the wildtype archaeal polB enzymes failed to polymerize over even five RNA bases (FIG. 1A). The DNA specificity of these polymerases has likely been driven by evolutionary pressures, as these are presumed to be the genome replicating polymerase and contain mechanisms actively precluding RNA as a substrate (Greagg et al., 1999).

SUMMARY OF THE INVENTION

Embodiments of the disclosure encompass isolated enzymes that have proofreading activity and that have reverse transcriptase activity. Embodiments of the disclosure also encompass recombinant enzymes that have proofreading activity and that have reverse transcriptase activity. In specific embodiments, the enzymes are thermophilic or hyperthermophilic. In at least some aspects, the enzymes are derivatives of a wildtype enzyme, such as a wild-type polymerase. In certain cases, the enzymes are mutated in comparison to a particular polymerase, such as an Archaeal Family-B polymerase. In particular embodiments, the enzymes of the disclosure have proofreading activity and have reverse transcriptase activity, although the enzymes are mutant versions of an enzyme that lacked reverse transcriptase activity. Embodiments of the disclosure also concern evolved thermostable polymerase capable of reverse transcription (cDNA synthesis) and PCR amplification.

In particular embodiments, the enzymes are evolved from another polymerase. The evolved polymerase may be derived from a hyperthermophilic archaeal DNA polymerase, distinguished by its ability for high fidelity DNA synthesis due to a proofreading (error-correcting) domain. The native archaeal DNA polymerase does not utilize RNA as a template, preventing its use as a reverse transcriptase. Directed evolution of the polymerase, during development of embodiments herein, yielded a variant capable of efficient reverse transcriptase activity. This differs from current reverse transcriptases because of its hyperthermostability and its functional proofreading domain, leading to significantly increased fidelity of the reverse transcription reaction. Aspects of the disclosure regard enzymes derived from polymerases having structure(s) or regions that specifically blocked the use of RNA as a substrate but that have been manipulated (for example, by design) to be able to utilize RNA as a template.

Thus, embodiments of the disclosure include methods of generating enzymes that exhibit reverse transcription activity from enzymes that do not exhibit reverse transcription activity. Embodiments also encompass methods of using enzymes that exhibit reverse transcription activity that are derived from enzymes that do not exhibit reverse transcription activity.

The disclosed polymerases are the first proofreading reverse transcriptase, offering at least three fold improvement in fidelity over existing reverse transcriptases. The disclosed polymerases also efficiently perform long-range reverse transcription PCR (longer than 5 kilobase amplification) as a sole enzyme in the reaction. Specific embodiments of the disclosure provide enzymes that produce cDNA from an RNA template at high temperatures (e.g., >50° C., >55° C., >60° C., >65° C., or higher). Thus, particular enzymes of the disclosure have the following characteristics: high themostability, the ability to reverse transcribe RNA templates, including long RNA templates; and proofreading. In certain embodiments, the enzymes may be utilized in polymerase chain reaction. In some embodiments, the enzymes may utilize DNA, RNA, modified DNA, modified RNA, or other nucleotide polymers as templates. In some embodiments, the enzymes are capable of utilizing templates comprising modifications such as the following: T-Fluoro, 2'-O-methyl, 2'-Amino, 2'-Azido, a-L-threofuranosyl nucleic acid (TNA), 1,5-anhydrohexitol nucleic acids (HNAs), cyclohexenyl nucleic acids (CeNAs), 2'-O,4'-C-methylene-b-Dribonucleic acids [locked nucleic acids (LNAs)], arabinonucleic acids (ANAs), or 2'-fluoro-arabinonucleic acids (FANAs). In some embodiments, the enzymes herein produce a DNA polymer from DNA monomers (e.g., deoxyadenosine triphosphate, deoxycytidine triphosphate, deoxyguanosine triphosphate, and deoxythymidine triphosphate) using a suitable nucleic acid template (e.g., DNA, RNA, modified DNA, modified RNA, other nucleotide polymers, etc.). In some embodiments, the enzymes herein are not capable of producing a non-DNA polymer (e.g., RNA, modified DNA, modified RNA, other nucleotide polymers, etc.) from a DNA template nor from another nucleic acid template (e.g., RNA, modified DNA, modified RNA, other nucleotide polymers, etc.). In further aspects, an enzyme of the embodiments is active on a 2'-O-methyl DNA template.

In particular embodiments, the enzymes comprise one or more additional domains, such as one or more polymerization enhancing domains. The additional domain may have activity as a DNA clamp, although in cases of the disclosure the clamp applies to any template that the enzyme can use. In certain embodiments the additional domain is able to bind nucleotide polymers. In specific embodiments, the additional domain comprises all or a portion of one or more of DNA-binding protein 7d (Sso7d), Proliferating cell nuclear antigen (PCNA), helicase, single stranded binding proteins, bovine serum albumin (BSA), and one or more affinity tags.

Embodiments of the disclosure also concern methods of generating the enzymes of the disclosure. In specific embodiments, the methods concern directed evolution of a new family of proofreading reverse transcriptases. In specific embodiments, reverse transcription compartmentalized self-replication is utilized with primers that comprise one or more RNA bases such that when the primer primes polymerization to transcribe the polymerase in question (being tested for reverse transcriptase activity), the resultant polymerase (each compartmentalized in a separate vessel) can only utilize the RNA-comprising strand as a template if it is capable of reverse transcription activity. The pool of mutated polymerases from which to test the members for reverse transcription activity may be generated by any suitable mutation methods.

Methods of using the enzymes of the disclosure for a variety of applications are encompassed in the disclosure. Methods related to sequencing of nucleic acids may be performed. For example, methods of converting mRNA into cDNA may be performed with enzymes of the disclosure, as are methods of direct RNA sequencing without a cDNA intermediate. Enzymes of the disclosure allow for methods of facilitating reverse transcription of RNAs comprising stable secondary structures. In certain aspects, the enzymes are utilizable in next-generation DNA/RNA sequencing technologies.

Compositions and methods of the disclosure provide for more extensive and accurate copying of any RNA population into cDNA, and hence a more accurate record of the molecules in that RNA population; this facilitates processes that rely on mRNA molecules, including at least NextGen Sequencing that relies on mRNA templates (i.e., RNASeq).

Embodiments of the disclosure include enzymes that have reverse transcriptase activity and are derived from recombinant Archaeal Family-B polymerases. The enzymes may also comprise proofreading activity and/or thermophilic or hyperthermophilic activity. As used herein, a transcriptase activity refers to an enzyme capable of polymerizing more than 5, 10, 15, 20, 50, 75, 100, 200 or more nucleotides from a particular template. Thus, in some aspects, an enzyme of the embodiments is able to polymerize more than 5 nucleotides from a RNA or 2'-OMethyl DNA template.

Embodiments of the disclosure concern a recombinant Archaeal Family-B-derived polymerase that is capable of transcribing a template that is RNA, modified DNA, or modified RNA. The modified DNA or modified RNA may be modified at the 2' position of a sugar of a component of the template. In specific cases, the modified DNA or modified RNA comprise a modification selected from the group consisting of 2'-Fluoro, 2'-O-methyl, 2'-Amino, 2'-Azido, a-L-threofuranosyl nucleic acid (TNA), 1,5-anhydrohexitol nucleic acids (HNAs), cyclohexenyl nucleic acids (CeNAs), T-0,4'-C-methylene-b-Dribonucleic acids [locked nucleic acids (LNAs)], arabinonucleic acids (ANAs), and 2'-fluoro-arabinonucleic acids (FANAs). In some cases, the polymerase has proofreading activity and/or the polymerase has thermophilic or hyperthermophilic activity. In further aspects, a polymerase of the embodiments lacks proofreading (3'-5' exonuclease) activity.

In particular embodiments, a polymerase within the scope herein has one or more mutations compared to a wild-type or other natural Archaeal Family-B polymerase. The polymerase may have one or more mutations compared to wild-type KOD polymerase. The one or more mutations are in a region of the polymerase that induces stalling at uracil residues; one or more mutations are in a region that recognizes the 2' hydroxyl of template RNAs; one or more mutations are in a region that directly acts with a template strand; one or more mutations are in a region for secondary shell interactions; one or more mutations are in a template recognition interface region; one or more mutations are in a region for recognizing an incoming template; one or more mutations are in an active site region; and/or one or more mutations are in a post-polymerization region, in specific embodiments. In some cases, a mutation is in a region or position in which the polymerase recognizes the 2' hydroxyl of a template RNA. At least one mutation may be an amino acid substitution, in at least some cases.

In certain embodiments, a polymerase has an amino acid sequence that is at least 70%, 75%, 80%, 85%, 90%, 95%, 97%, 98%, or 99% identical to the amino acid sequence of SEQ ID NO:1. In some embodiments, a polymerase comprises at least one amino acid substitution relative to SEQ ID NO:1. In some embodiments, the at least one amino acid substitution corresponds to an amino acid at positions 384, 389, 664, 493, 97, 521, 711, or 735 of SEQ ID NO:1, or any suitable combinations thereof. In certain aspects, a polymerase of embodiments herein comprises one or more of the amino acid substitutions provided in Table A. In specific embodiments, the amino acid substitution corresponds to an amino acid at position 97. In some cases, there is an amino acid substitution that corresponds to an amino acid at position 490, 587, 137, 118, 514, 381, 38, 466, 734, or a combination thereof. In some embodiments, the amino acid substitution corresponding to position 384 may be to a histidine residue or an isoleucine residue. In some embodiments, the amino acid substitution corresponding to position 384 may be to a phenylalanine residue, a leucine residue, an alanine residue, a cysteine residue, a serine residue, a histidine residue, an isoleucine residue, a methionine residue, an asparagine residue, or a glutamine residue. In some embodiments, the amino acid substitution corresponding to position 389 may be an isoleucine residue or a leucine residue. In some embodiments, the amino acid substitution corresponding to position 389 may be to a methionine residue, a phenylalanine residue, a threonine residue, a tyrosine residue, a glutamine residue, an asparagine residue, or a histidine residue. In some embodiments, the amino acid substitution corresponding to position 664 may be to a lysine residue or a glutamine residue. In further aspects, a polymerase of the embodiments does not comprise a substitution as the position corresponding to position 664. In some embodiments, the amino acid substitution corresponding to position 493 may be to a leucine residue, a cysteine residue, or a phenylalanine residue. In some embodiments, the amino acid substitution corresponding to position 493 may be to an isoleucine residue, a valine residue, an alanine residue, a histidine residue, a threonine residue, or a serine residue. In some embodiments, the amino acid substitution corresponding to position 97 may be to any amino acid residue other than arginine. In some embodiments, the amino acid substitution corresponding to position 521 may be to a leucine. In some embodiments, the amino acid substitution corresponding to position 521 may be to a phenylalanine residue, a valine residue, a methionine residue, or a threonine residue. In some embodiments, the amino acid substitution corresponding to position 711 may be to a valine residue, a serine residue, or an arginine residue. In some embodiments, the amino acid substitution corresponding to position 711 may be to a leucine residue, a cysteine residue, a threonine residue, an arginine residue, a histidine residue, a glutamine residue, a lysine residue, or a methionine residue. In some embodiments, the amino acid substitution corresponding to position 735 may be to a lysine residue. In some embodiments, the amino acid substitution corresponding to position 735 may be to an arginine residue, a glutamine residue, an arginine residue, a tyrosine residue, or a histidine residue. In some embodiments, the amino acid substitution corresponding to position 490 may be to a threonine residue. In some embodiments, the amino acid substitution corresponding to position 490 may be to a valine residue, a serine residue, or a cysteine residue. In some embodiments, the amino acid substitution corresponding to position 587 may be to a leucine residue or an isoleucine residue. In some embodiments, the amino acid substitution corresponding to position 587 may be to an alanine residue, a threonine residue, or a valine residue. In some embodiments, the amino acid substitution corresponding to position 137 may be to a leucine residue or an isoleucine residue. In some embodiments, the amino acid substitution corresponding to position 137 may be to an alanine residue, a threonine residue, or a valine residue. In some embodiments, the amino acid substitution corresponding to position 118 may be to an isoleucine residue. In some embodiments, the amino acid substitution corresponding to position 118 may be to a methionine residue, a valine residue, or a leucine residue. In some embodiments, the amino acid substitution corresponding to position 514 may be to an isoleucine residue. In some embodiments, the amino acid substitution corresponding to position 514 may be to a valine residue, a leucine residue, or a methionine residue. In some embodiments, the amino acid substitution corresponding to position 381 may be to a histidine residue. In some embodiments, the amino acid substitution corresponding to position 381 may be to a serine residue, a glutamine residue, or a lysine residue. In some embodiments, the amino acid substitution corresponding to position 38 may be to a leucine residue or an isoleucine residue. In some embodiments, the amino acid substitution corresponding to position 38 may be to a valine residue, a methionine residue, or a serine residue. In some embodiments, the amino acid substitution corresponding to position 466 may be to an arginine residue. In some embodiments, the amino acid substitution corresponding to position 466 may be to a glutamate residue, an aspartate residue, or a glutamine residue. In some embodiments, the amino acid substitution corresponding to position 734 may be to a lysine residue. In some embodiments, the amino acid substitution corresponding to position 734 may be to an arginine residue, a glutamine residue, or an asparagine residue.

In certain cases, a polymerase has an amino acid sequence that is at least 70%, 75%, 80%, 85%, 90%, 95%, 97%, 98%, or 99% identical to the amino acid sequence of SEQ ID NO:1 and the polymerase has an amino acid substitution at one or more of the following positions corresponding to SEQ ID NO:1: R97; Y384; V389; Y493; F587; E664; G711; and W768. In certain embodiments, the polymerase has one or more of the following amino acid substitutions corresponding to SEQ ID NO:1: R97M; Y384H; V389I; Y493L; F587L; E664K; G711V; and W768R, in some aspects.

In specific embodiments, a polymerase has an amino acid sequence that is at least 70%, 75%, 80%, 85%, 90%, 95%, 97%, 98%, or 99% identical to the amino acid sequence of SEQ ID NO:1 and the polymerase has an amino acid substitution at one or more of the following positions corresponding to SEQ ID NO:1: F38; R97; K118; R381; Y384; V389; Y493; T514; F587; E664; G711; and W768. In some embodiments, the polymerase has one or more of the following amino acid substitutions corresponding to SEQ ID NO:1: F38L; R97M; K118I; R381H; Y384H; V389I; Y493L; T514I; F587L; E664K; G711V; and W768R.

In particular aspects, the polymerase has an amino acid sequence that is at least 70%, 75%, 80%, 85%, 90%, 95%, 97%, 98%, or 99% identical to the amino acid sequence of SEQ ID NO:1 and wherein the polymerase has an amino acid substitution at one or more of the following positions corresponding to SEQ ID NO:1: F38; R97; K118; M137; R381; Y384; V389; K466; Y493; T514; F587; E664; G711; and W768. The polymerase may have one or more of the following amino acid substitutions corresponding to SEQ ID NO:1: F38L; R97M; K118I; M137L; R381H; Y384H; V389I; K466R; Y493L; T514I; F587L; E664K; G711V; and W768R.

In certain embodiments, the polymerase has an amino acid sequence that is at least 70%, 75%, 80%, 85%, 90%, 95%, 97%, 98%, or 99% identical to the amino acid sequence of SEQ ID NO:1 and wherein the polymerase has an amino acid substitution at one or more of the following positions corresponding to SEQ ID NO:1: F38; R97; K118; M137; R381; Y384; V389; K466; Y493; T514; I521; F587; E664; G711; N735; and W768. The polymerase may have one or more of the following amino acid substitutions corresponding to SEQ ID NO:1: F38L; R97M; K118I; M137L; R381H; Y384H; V389I; K466R; Y493L; T514I; I521L; F587L; E664K; G711V; N735K; and W768R.

In further aspects, a polymerase of the embodiments lacks 3' to 5' exonuclease activity. Methods for inactivating exonuclease activity via engineered disruption of the exonuclease domain are well known in the art (see, e.g., Nishioka et al., 2001, incorporated herein by reference). For example, in some aspects, a polymerase of the embodiments, has an amino acid sequence that is at least 70%, 75%, 80%, 85%, 90%, 95%, 97%, 98%, or 99% identical to the amino acid sequence of SEQ ID NO:1 and has an amino acid substitution corresponding to N210 (e.g., N210D), to eliminate 3' to 5' exonuclease activity. In further aspects, has an amino acid sequence that is at least 70%, 75%, 80%, 85%, 90%, 95%, 97%, 98%, or 99% identical to the amino acid sequence of SEQ ID NO:1 and has an amino acid substitution corresponding to D141 and E143 (e.g., D141A and E143A), to eliminate 3' to 5' exonuclease activity. In preferred aspects, a polymerase of the embodiments lacking a 3' to 5' exonuclease activity further comprises one or more of the amino acid substitution of Table A. Other amino acid substitutions that disrupt the 3' to 5' exonuclease activity are within the scope herein.

There is provided herein a recombinant Archaeal Family-B polymerase that transcribes a template that is RNA and has one or more genetically engineered mutations compared to a wild-type Archaeal Family-B polymerase, the polymerase having an amino acid sequence at least 70%, 75%, 80%, 85%, 90%, 95%, 97%, 98%, or 99% identical to SEQ ID NO: 1 and in which one or more amino acid residues at a position selected from the group consisting of positions Y493, Y384, V389, I521, E664 and G711 in the amino acid sequence shown in SEQ ID NO:1 or at a position corresponding to any of these positions, are substituted with another amino acid residue. In some cases, the polymerase comprises an amino acid substitution corresponding to position Y493 to a leucine residue or a cysteine residue. In some cases, the polymerase comprises an amino acid substitution corresponding to position Y493 to a leucine residue. In some cases, the polymerase comprises an amino acid substitution corresponding to position Y384 to a phenylalanine residue, a leucine residue, an alanine residue, a cysteine residue, a serine residue, a histidine residue, an isoleucine residue, a methionine residue, an asparagine residue, or a glutamine residue. In some cases, the polymerase comprises an amino acid substitution corresponding to position Y384 to a histidine residue or an isoleucine residue. In some cases, the polymerase comprises an amino acid substitution corresponding to position V389 to a methionine residue, a phenylalanine residue, a threonine residue, a tyrosine residue, a glutamine residue, an asparagine residue, or a histidine residue. In some cases, the polymerase comprises an amino acid substitution corresponding to position V389 to an isoleucine residue. In some cases, the polymerase comprises an amino acid substitution corresponding to position I521 to a leucine. In some cases, the polymerase comprises an amino acid substitution corresponding to E664 is to a lysine residue. In some cases, the polymerase comprises an amino acid substitution corresponding to position G711 to a leucine residue, a cysteine residue, a threonine residue, an arginine residue, a histidine residue, a glutamine residue, a lysine residue, or a methionine residue. In some cases, the polymerase comprises an amino acid substitution corresponding to position G711 to a valine residue. In some cases, the polymerase comprises an amino acid substitution at a position R97 in the amino acid sequence shown in SEQ ID NO:1 with another amino acid residue. In some cases, the polymerase comprises one or more amino acid residues at a position selected from the group consisting of positions A490, F587, M137, K118, T514, R381, F38, K466, E734 and N735 in the amino acid sequence shown in SEQ ID NO:1 or at a position corresponding to any of these positions, which is substituted with another amino acid residue. In some cases, the polymerase has proofreading activity. In some case, the polymerase lacks proofreading activity. In some cases, the polymerase has thermophilic activity. In some cases, the polymerase is capable transcribing at least 10 nucleotides from a RNA template. In some cases, the polymerase is capable of transcribing a template that is 2'-OMethyl DNA. In some cases, the polymerase is capable transcribing at least 5 or at least 10 nucleotides from a 2'-OMethyl DNA template.

In some aspects a nucleic acid molecule is provided that encodes a polymerase according to any of the embodiments described herein. Likewise, a method is provided for using a polymerase of the embodiments comprising comprising the step of contacting the polymerase to a nucleic acid template under suitable conditions to produce a polymerized molecule. In some cases the nucleic acid template is RNA, DNA or is 2'-OMethyl DNA.

In certain cases, polymerases further comprise an additional domain, such as one that does not itself take part in polymerization but has polymerization enhancing activity. In a specific embodiment, the additional domain comprise part or all of DNA-binding protein 7d (Sso7d), Proliferating cell nuclear antigen (PCNA), helicase, single stranded binding proteins, bovine serum albumin (BSA), one or more affinity tags, a label, and a combination thereof.

In one embodiment, provided herein there is a method of using a polymerase according to the embodiments, comprising the step of subjecting the polymerase to a nucleic acid template under suitable conditions to produce a polymerized molecule. The template may be RNA or DNA or modified RNA or modified DNA. In specific embodiments, the method lacks generation of a cDNA molecule. In specific embodiments, the method provides sequence information for at least part of the template. In certain cases, the polymerized molecule is sequenced. The nucleic acid template may be part of a population of nucleic acid molecules, such as a genome or transcriptome, for example. In further aspects, a method of the embodiments comprises contacting a polymerase described herein with an RNA template to produce a cDNA. In further aspects, the method further comprises amplifying at least a portion of the cDNA molecules to polymerase chain reaction (PCR). In certain aspects, a polymerase of the embodiments is used both to generate the cDNA and amplify the cDNA. In certain specific aspects, a method herein is used to produce cDNA from two or more distinct RNA molecules (e.g., from a single cell). For example, the method can be used to produce cDNA, and optionally amplified DNA copies, of antibody VH and VL sequence or T-cell receptor chains (TCR). In certain aspects, the method is used to produce paired antibody VH and VL coding sequences or paired TCR coding sequences.

In one embodiment, there is a method of selecting an enzyme with reverse transcriptase activity, comprising the steps of: a) providing a population of nucleic acids that comprise a region that encodes a polymerase, wherein the polymerase may or may not have reverse transcriptase activity, wherein the region that encodes the polymerase is flanked by a region in the nucleic acid to which a primer binds, wherein the primer comprises one or more RNA nucleotide bases; b) subdividing the pool of nucleic acids into separate vessels, such that each vessel comprises a nucleic acid member of the population and the polymerase encoded by the nucleic acid member; c) subjecting the nucleic acid member and the polymerase to suitable conditions to allow polymerization from the primer to occur to produce a RNA base-comprising template; and d) assaying for polymerization of a nucleic acid molecule using the RNA base-comprising template as template, wherein when there is polymerization, the polymerase has reverse transcriptase activity. In some cases, the method further comprises the step of amplifying the RNA base-comprising template using the polymerase and/or amplifying molecules polymerized from the RNA base-comprising template using the polymerase. In some embodiments, the method further comprises the step of producing the population of nucleic acids that comprise a region that encodes the polymerase. The population may be produced by introducing one or more mutations in nucleic acid that encodes the polymerase. In specific embodiments, the one or more mutations are introduced in the nucleic acid randomly. The one or more mutations may be introduced by polymerase chain reaction. The one or more mutations may be introduced in the nucleic acid in a directed manner. In specific embodiments, nucleic acid in which one or more mutations are introduced corresponds to that which encodes an Archaeal Family-B polymerase that lacks reverse transcriptase activity, such as the Archaeal Family-B polymerase is KOD polymerase. In specific embodiments, the primer comprises more than one RNA nucleotide base, and the primer may comprise all RNA nucleotide bases. In specific embodiments, the polymerase has reverse transcriptase activity and is subject to sequencing.

In another embodiments, a kit is provided that comprises a polymerase of the disclosure. In specific cases, the kit comprises one or more of the following: vector(s), nucleotides, buffers, salts, and instructions.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1C shows directed evolution of reverse transcriptase function in Archaeal family-B polymerases. 1A, Primer extension reveals Archaeal polB are sensitive to RNA in the template strand, stalling polymerization with several repeat RNAs. 1B, Framework for the directed evolution of hyperthermostable reverse transcriptase using reverse transcription compartmentalized self-replication (RTCSR). Libraries of polymerase mutants are created, expressed in E. coli and subjected to emulsion PCR. Primers flanking the polymerase are designed with a variable number of RNA bases separating the plasmid annealing portion from the recovery tag, allowing a tunable stringency over the course of evolution. Recovery PCR specifically amplifies polymerases with reverse transcriptase activity. 1C, Structural heat map of conserved residues found by deep sequencing over the RTCSR process. Mutated residues that are more conserved are colored incrementally darker shades. Amino acid residues that were mutated in over 50% of the population were labeled. Figure was adapted from KOD structure PDB 4K8Z.

DETAILED DESCRIPTION

I. Enzymes of the Disclosure

Figures 2A, 2B:
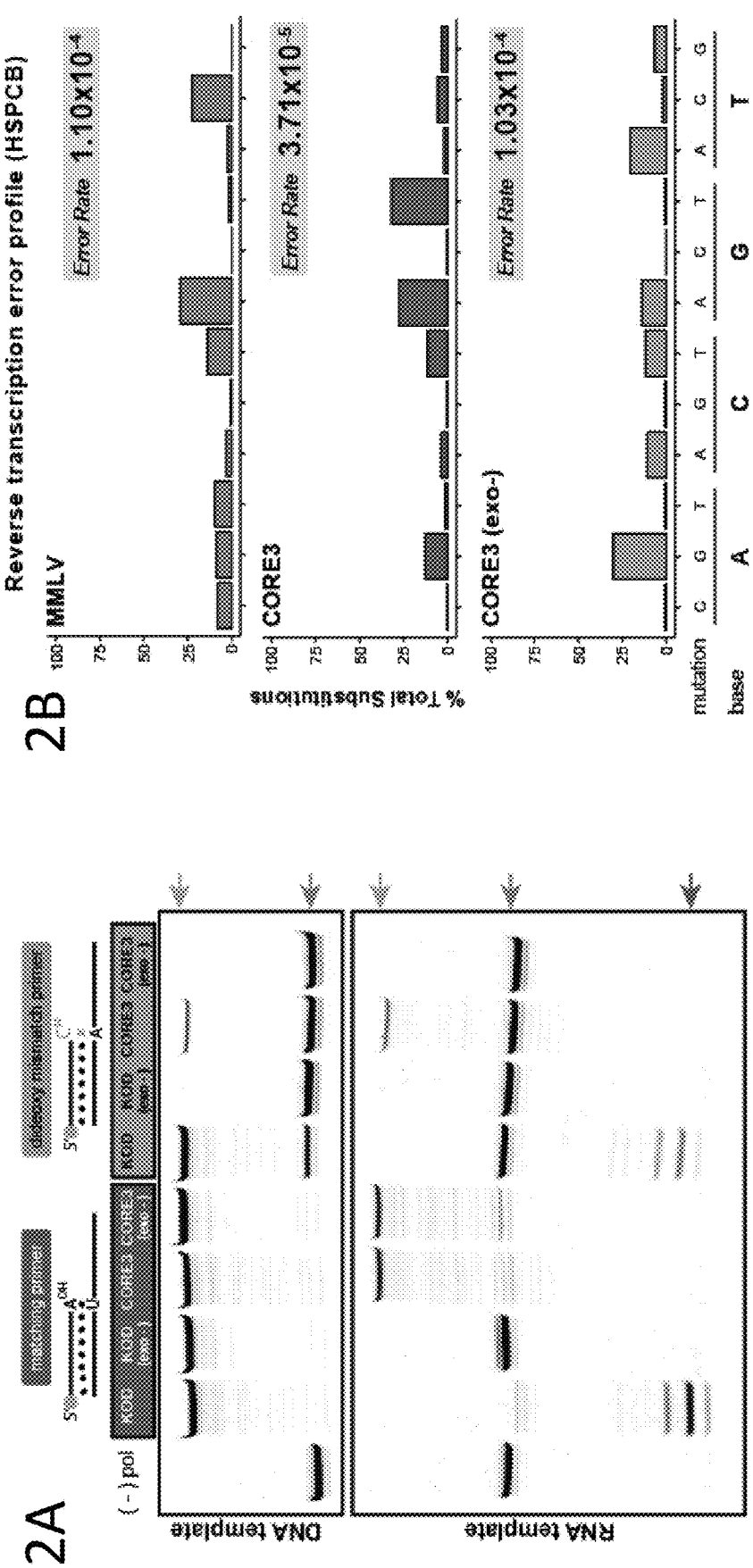
FIGS. 2A-2B shows that engineered reverse transcriptases contain active proofreading domains. 2A, Single cycle primer extension reaction of KOD and CORE3 polymerases and their proofreading deficient counterparts, on both DNA and RNA substrates. Extension reactions were performed with both matched 3' primer:templates (purple) or a 3' dideoxy mismatch (orange), which must be excised by proofreading before extension can proceed. The primer is denoted by a gray arrow, extended product in green, and exonuclease digested primer in red. 2B, Deep sequencing of reverse transcription reaction on HSPCB gene using the SSCS technique. The error rate was determined by dividing the sum of base substitutions and indel formation by the total number of bases sequenced. The error profile of reverse transcription is shown as a percentage of all possible mutations.

Despite the critical role that reverse transcriptase plays in molecular biology, inherent limitations exist in known reverse transcriptases—they are error prone due to their lack of a proofreading domain. The present disclosure concerns proofreading reverse transcriptases, at least some of which that are thermophilic or hyperthermophilic. In particular embodiments, the disclosure concerns the directed evolution of a novel family of reverse transcriptases derived from a high fidelity hyperthermophilic Archaeal Family-B polymerase. Over the evolutionary process described herein, the template interface of the polymerase was dramatically mutated, allowing generation of enzymes that comprised efficient RNA directed DNA polymerase activity. Embodiments of the engineered polymerase are capable of single enzyme reverse transcription-PCR of long RNAs (e.g., >5 kb) at high temperatures (e.g., 68° C.). In some embodiments, the polymerase retains an active proofreading domain and achieves the highest in vitro fidelity reported. Kinetic analyses demonstrated roughly equal polymerization efficiency on both DNA and RNA templates, marking a massive shift in specificity compared to the parental polymerase. The polymerase was also shown to be easily incorporated into current RNA-Seq platforms, as well as allowing direct RNA sequencing without a cDNA intermediate. The unique properties of this new family of polymerase enables a deeper and more accurate understanding of transcriptomics and drive future biotechnology innovations.

In some embodiments, exemplary enzymes of the disclosure have the ability to generate DNA from a template that comprises RNA bases, either in part or in its entirety. In specific embodiments, the enzymes are recombinant enzymes. In some embodiments, the enzymes have the ability to use RNA as a template when their parent enzyme from which they were derived (by mutation) lacked such ability. In specific cases, the enzymes that acquire reverse transcriptase activity are able to recognize alternative bases or sugars in a template strand (compared to an enzyme that can only recognize DNA as a template), such as by allowing recognition of a template having uracil instead of thymine and having variability at the 2' position in the ribose ring.

The enzymes of the present disclosure make it easier to melt RNA structure and generate cDNA copies, in specific embodiments. Although there are other commercially available reverse transcriptases with modest thermostability, the enzymes of the present disclosure have much higher thermostability (e.g., thermostability at temperatures above 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., or more) and have proofreading activity. In specific embodiments, the enzymes of the present disclosure are more processive and/or more primer-dependent, resulting in less promiscuity in generating an accurate cDNA imprint of a mRNA population, for example. Because of their proofreading domain, the enzymes of the present disclosure generate fewer mutations than other enzymes and provide a more accurate representation of the RNAs present in a given population (including, for example, a sample from one or more individuals, environments, and so forth).

At least some enzymes of the disclosure encompass proofreading activity, which may be defined herein as the ability of the enzyme to recognize an incorrect base pair, reverse its direction and excise the mismatched base, followed by insertion of the correct base. Enzymes of the disclosure may be referred to as comprising 3'-5' exonuclease activity. Although testing a particular enzyme for proofreading activity may be achieved in a variety of ways, in specific embodiments the enzyme is tested by dideoxy-mismatch PCR that necessitates removal of a 3' deoxy mismatch primer prior to polymerization or primer extension reactions with 3' terminal deoxy mismatches.

Although certain enzymes of the disclosure may be characterized as reverse transcriptases, in particular aspects the enzymes can utilize DNA, RNA, modified DNA, and/or modified RNA as a template. Modified DNA and RNA may be referred to as information nucleotide-comprising polymers that can be replicated enzymatically that contain altered chemical modifications to the backbone, sugar or base. In specific cases, the modified DNA or RNA is modified at the 2' position of a sugar of a component of the template. Particular embodiments encompass recombinant Archaeal Family-B polymerases that transcribe a template that is DNA, RNA, modified DNA, or modified RNA.

The enzymes of the disclosure may be generated using a starting polymerase that lacks reverse transcriptase activity, and in specific embodiments, that starting polymerase is an Archaeal Family-B polymerase, such as KOD polymerase. Any number of mutations may be generated from the starting polymerase and tested for using methods of the disclosure. In specific embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more mutations are incorporated into a polymerase that lacks reverse transcriptase activity such that the entirety of mutations (or a sub-combination thereof) are responsible for imparting reverse transcriptase activity to the polymerase that originally lacked it. The mutations may be of any kind, including amino acid substitution(s), deletion(s), insertion(s), inversion(s), and so forth. In specific embodiments, the mutation is a single amino acid change, and the change may or may not be conservative. Although in some cases the amino acid substitution mutation must be to a certain amino acid, in other cases the mutation may be to any amino acid. Embodiments within the scope herein are not limited by the means of generating/designing the various enzymes. While some enzymes are designed via mutations to a starting polymerase, embodiments herein are not limited to any particular mechanism of action and an understanding of the mechanism of action is not necessary to practice such embodiments.

In certain embodiments, an enzyme of the disclosure has a specific amino acid sequence identity compared to a given enzyme, for example a wild-type Archaeal Family-B polymerase, such as KOD polymerase (including, for example, SEQ ID NO:1). In specific embodiments, the enzyme has an amino acid sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to the amino acid sequence of SEQ ID NO:1. An enzyme of the disclosure may be of a certain length, including at least or no more than 600, 625, 650, 675, 700, 725, 750, 755, 760, 765, 770, 775, 780, 781, 782, 783, or 784 amino acids in length, for example. The enzyme may or may not be labeled. The enzyme may be further modified, such as comprising new functional groups such as phosphate, acetate, amide groups, or methyl groups, for example. The enzymes may be phosphorylated, glycosylated, lapidated, carbonylated, myristoylated, palmitoylated, isoprenylated, farnesylated, alkylated, hydroxylated, carboxylated, ubiquitinated, deamidated, contain unnatural amino acids by altered genetic codes, contain unnatural amino acids incorporated by engineered synthetase/tRNA pairs, and so forth. The skilled artisan recognizes that post-translational modification of the enzymes may be detected by one or more of a variety of techniques, including at least mass spectrometry, Eastern blotting, Western blotting, or a combination thereof, for example.

Specific examples of enzymes of the disclosure include at least the following:

B11 reverse transcriptase (an example of a derivative of KOD polymerase that is a hyperthermophilic reverse transcriptase):

(SEQ ID NO: 2)
MILDTDYITEDGKPVIRIFKKENGEFKIEYDRTFEPYLYALLKDDSAIEE

VKKITAERHSTVVTVKRVEKVQKKFLGRSVEVWKLYFTHPQDVPAIMDKI

REHPAVIDIYEYDIPFAIRYLIDKGLVPMEGDEELKLLALDIGTPCHEGE

VFAEGPILMISYADEEGTRVITWRNVDLPYVDVLSTEREMIQRFLRVVKE

KDPDVLITYNGDNFDFAYLKKRCEKLGINFTLGREGSEPKIQRMGDRFAV

EVKGRIHFDLYPVIRRTVNLPIYTLEAVYEAVFGQPKEKVYAEEITTAWE

TGENLERVARYSMEDAKVTYELGKEFMPMEAQLSRLIGQSLWDVSRSSTG

NLVEWFLLRKAYERNELAPNKPDEKELARRHQSHEGGYIKEPERGLWENI

VYLDFRSLYPSIIITHNVSPDTLNREGCKEYDVAPQVGHRFCKDFPGFIP

SLLGDLLEERQKIKKRMKATIDPIERKLLDYRQRAIKILANSLYGYYGYA

RARWYCKECAESVIAWGREYITMTIKEIEEKYGFKLIYSDTDGFFATIPG

AEAETVKKKAMEFLKYINAKLPGALELEYEGFYKRGLFVTKKKYAVIDEE

GKITTRGLEIVRRDWSEIAKETQARVLEALLKDGDVEKAVRIVKEVTEKL

SKYEVPPEKLVIHKQITRDLKDYKATGPHVAVAKRLAARGVKIRPGTVIS

YIVLKGSGRIVDRAIPFDEFDPTKHKYDAEYYIENQVLPAVERILRAYGY

RKEDLWYQKTRQVGLSARLKPKGT

CORE3 reverse transcriptase (an example of a derivative of KOD polymerase that is a hyperthermophilic proofreading reverse transcriptase):

(SEQ ID NO: 3)
MILDTDYITEDGKPVIRIFKKENGEFKIEYDRTFEPYLYALLKDDSAIEE

VKKITAERHGTVVTVKRVEKVQKKFLGRPVEVWKLYFTHPQDVPAIMDKI

REHPAVIDIYEYDIPFAIRYLIDKGLVPMEGDEELKLLAFDIETLYHEGE

EFAEGPILMISYADEEGARVITWKNVDLPYVDVVSTEREMIKRFLRVVKE

KDPDVLITYNGDNFDFAYLKKRCEKLGINFALGRDGSEPKIQRMGDRFAV

EVKGRIHFDLYPVIRRTINLPTYTLEAVYEAVFGQPKEKVYAEEITTAWE

TGENLERVARYSMEDAKVTYELGKEFLPMEAQLSRLIGQSLWDVSRSSTG

NLVEWFLLRKAYERNELAPNKPDEKELARRHQSHEGGYIKEPERGLWENI

VYLDFRSLYPSIIITHNVSPDTLNREGCKEYDVAPQVGHRFCKDFPGFIP

SLLGDLLEERQKIKKRMKATIDPIERKLLDYRQRAIKILANSLYGYYGYA

RARWYCKECAESVIAWGREYLTMTIKEIEEKYGFKVIYSDTDGFFATIPG

ADAETVKKKAMEFLKYINAKLPGAELELEYEGFYKRGLFVTKKKYAVIDE

EGKITTRGLEIVRRDWSEIAKETQARVLEALLKDGDVEKAVRIVKEVTEK

LSKYEVPPEKLVIHKQITRDLKDYKATGPHVAVAKRLAARGVKIRPGTVI

SYIVLKGSGRIVDRAIPFDEFDPTKHKYDAEYYIEKQVLPAVERILRAFG

YRKEDLRYQKTRQVGLSARLKPKGT

In particular aspects, the enzymes of the disclosure have one or more mutations in at least one of the following regions of a particular polymerase (here, as it corresponds to SEQ ID NO:1): residues (1-130 and 338-372 is N-terminal domain); (131-338 is exonuclease domain); (448-499 is finger domain); (591-774 is thumb domain); (374-447 and 500-590 is palm domain).

In certain embodiments, the enzymes of the disclosure have mutations at particular amino acids (the position of which corresponds to SEQ ID NO:1, in certain examples) and, in some cases particular residues are the substituted amino acid at that position. The table below provides an example of a list of certain mutations that may be present in the disclosure, and in specific embodiments a combination of mutations is utilized in the enzyme.

TABLE A

Amino acid substitutions for polymerase enzymes of the embodiments

| KOD Position | Mutation for RT activity | Possible other mutations |
|---|---|---|
| Y384 | H, I | F, L, A C, S, H, I, M, N, Q |
| V389 | I, L | M, F, T, Y, Q, N, H |
| E664 | K, Q | |
| Y493 | L, C, F | I, V, A, H, T, S |
| R97 | Any mutation | |
| I521 | L | F, V, M, T |
| G711 | V, S, R | L, C, T, N, H, Q, K, M |
| N735 | K | R, Q, N, Y, H |
| A490 | T | V, S, C |
| F587 | L, I | A, T, V |
| M137 | L, I | A, T, V |
| K118 | I | M, V, L |
| T514 | I | V, L, M |
| R381 | H | S, Q, K |
| F38 | L, I | V, M, S |
| K466 | R | E, D, Q |
| E734 | K | R, Q, N |

In at least some cases, the enzymes have a mutation at R97 as it corresponds to SEQ ID NO:1. In some cases, two or more, three or more, four or more, five or more, six or more, seven or more, eight or more, nine or more, ten or more, eleven or more, twelve or more, thirteen or more, fourteen or more, fifteen or more, or sixteen or more mutations from this table are present in an enzyme of the disclosure. In specific embodiments, the following combinations are included alone or with one or more other mutations listed above or not listed above:

Y384 and V389; Y384 and E664; Y384 and Y493; Y384 and R97; Y384 and I521; Y384 and G711; Y384 and N735; Y384 and A490; V389 and E664; V389 and Y493; V389 and R97; V389 and I521; V389 and G711; V389 and N735; V389 and A490; E664 and Y493; E664 and R97; E664 and I521; E664 and G711; E664 and N735; E664 and A490; Y493 and R97; Y493 and I521; Y493 and G711; Y493 and N735; Y493 and A490; R97 and I521; R97 and G711; R97 and N735; R97 and A490; I521 and G711; I521 and N735; I521 and A490; G711 and N735; or G711 and A490. In at least some cases, one or more other mutations are combined with these specific combinations.

In specific embodiments, the polymerase has an amino acid substitution at one or more of the following positions corresponding to SEQ ID NO:1:

a) R97; Y384; V389; Y493; F587; E664; G711; and W768;

b) F38; R97; K118; R381; Y384; V389; Y493; T514; F587; E664; G711; and W768;

c) F38; R97; K118; M137; R381; Y384; V389; K466; Y493; T514; F587; E664; G711; and W768; or d) F38; R97; K118; M137; R381; Y384; V389; K466; Y493; T514; I521; F587; E664; G711; N735; and W768.

Any of the combinations in a), b), c), or d) may include A490, F587, M137, K118, T514, R381, F38, K466, and/or E734. In particular embodiments, the polymerase has one or more of the following specific amino acid substitutions corresponding to SEQ ID NO:1:

a) R97M; Y384H; V389I; Y493L; F587L; E664K; G711V; and W768R;

b) F38L; R97M; K118I; R381H; Y384H; V389I; Y493L; T514I; F587L; E664K; G711V; and W768R;

c) F38L; R97M; K118I; M137L; R381H; Y384H; V389I; K466R; Y493L; T514I; F587L; E664K; G711V; and W768R; or d) F38L; R97M; K118I; M137L; R381H; Y384H; V389I; K466R; Y493L; T514I; I521L; F587L; E664K; G711V; N735K; and W768R.

Any of the combinations in a), b), c), or d) may include A490, F587, M137, K118, T514, R381, F38, K466, and/or E734.

II. Generation of Recombinant Enzymes

Methods in the disclosure provide for the generation of enzymes (e.g., recombinant enzymes) that comprise reverse transcription activity and proofreading activity and, at least in some cases, are thermophilic or hyperthermophilic. The generation of the enzymes occurs upon manipulation of a parent polymerase that lacks at least reverse transcription activity. Although a variety of methods may be employed to achieve this end, in particular embodiments the methods utilize high throughput strategies to obtain mutant versions of a parent polymerase, thereby introducing new characteristic(s) to the resultant enzyme. In specific embodiments, directed evolution strategies are employed to produce development of a recombinant enzyme with reverse transcriptase activity from a DNA polymerase that normally lacks reverse transcriptase activity. Such differences between the recombinant enzyme and the parent DNA polymerase include development by the recombinant enzyme of the ability to use RNA as a template, such as by allowing the enzyme to recognize alternative bases or sugars in a template strand (for example, allowing recognition of a template comprising uracil instead of thymine and allowing variability at the 2' position in the ribose ring).

In particular embodiments, enzymes of the disclosure are generated from manipulation of a DNA polymerase that normally lacks reverse transcriptase activity by randomly (or in a directed manner, in alternative embodiments) mutating the polymerase at a region, location, or residue(s) associated with one or more of the following: (1) template entry to the enzyme; (2) polymerization at the active site; and (3) formation and/or maintaining of the nascent duplex.

Production of the mutant enzymes may occur by any suitable means, and following their generation they may be tested for the ability to reverse transcribe one or more test templates. Examples of randomly (for example) introducing mutations includes by error-prone PCR, or gene shuffling. Directed mutation may occur by site-directed mutagenesis, for example.

Figure 12:
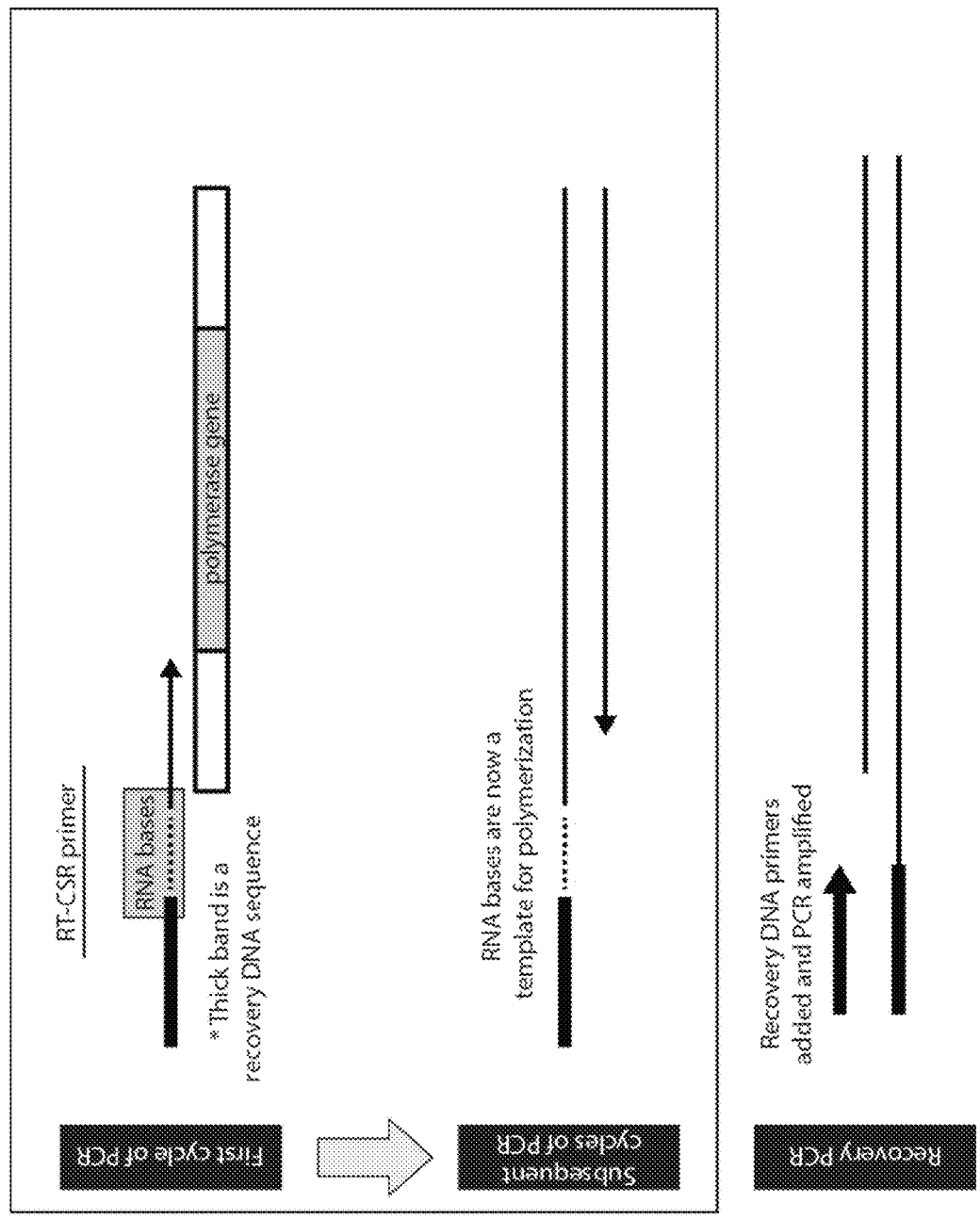
FIG. 12. Schematic demonstrates an example of directed evolution of reverse transcriptases.

In specific embodiments, a directed evolution strategy to test new enzymes employs reverse transcription compartmentalized self-replication (RT-CSR). As described herein, methods are employed for utilizing a feedback loop comprising a polymerase in an environment that allows replication of only the nucleic acid that encodes it. In the present case, primers comprising one or more RNA bases are utilized such that the expressed polymerase can only be extracted if it is able to recognize a template that comprises RNA nucleotides (see FIG. 12, for example). A pool of candidate polymerases that may or may not comprise reverse transcriptase activity may be tested with RT-CSR, with each compartment (or vessel) comprising a different candidate polymerase.

The method of testing for candidate polymerases with reverse transcriptase activity may also be a step in methods of generating the candidate polymerases. In some embodiments, candidate polymerases that may or may not have reverse transcriptase activity are produced through mutation of a known polymerase that lacks reverse transcriptase activity. The mutations may be incorporated into the polymerase-encoding nucleic acid molecules by any suitable methods to produce candidate polymerases with reverse transcriptase activity.

In specific embodiments, a parent polymerase that lacks reverse transcriptase activity and that is used for mutating is an Archaeal Family-B polymerase, and specific examples include at least DNA polymerases from *Thermococcus gorgonarius; Pyrococcus furiosus; Pyrococcus kondakaraensis* (also known as *Thermococcus kodakarensis*); *Desulfurococcus* strain *Tok; Thermococcus* sp. 9° N-7; *Thermococcus litoralis; Methanococcus voltae; Pyrobaculum islandicum; Archaeoglobus fulgidus; Cenarchaeaum symbiosum; Sulfolobus acidocaldarius; Sulfurisphaera ohwakuensis; Sulfolobus solfataricus; Pydrodictium occultum;* and *Aeropyrum pernix*. Enzymes of the disclosure may have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to the amino acid sequence of a polymerase from one of the above-listed organisms. Although any DNA polymerase may be used as the parent enzyme to which mutations are imparted to obtain proofreading reverse transcriptases, in some cases the enzyme used for modification is KOD polymerase from *Pyrococcus kodakaraensis*. The protein sequence for the wild-type enzyme is a follows:

(SEQ ID NO: 1)
MILDTDYITEDGKPVIRIFKKENGEFKIEYDRTFEPYFYALLKDDSAIEE

VKKITAERHGTVVTVKRVEKVQKKFLGRPVEVWKLYFTHPQDVPAIRDKI

REHPAVIDIYEYDIPFAKRYLIDKGLVPMEGDEELKMLAFDIETLYHEGE

EFAEGPILMISYADEEGARVITWKNVDLPYVDVVSTEREMIKRFLRVVKE

KDPDVLITYNGDNFDFAYLKKRCEKLGINFALGRDGSEPKIQRMGDRFAV

EVKGRIHFDLYPVIRRTINLPTYTLEAVYEAVFGQPKEKVYAEEITTAWE

TGENLERVARYSMEDAKVTYELGKEFLPMEAQLSRLIGQSLWDVSRSSTG

NLVEWFLLRKAYERNELAPNKPDEKELARRRQSYEGGYVKEPERGLWENI

VYLDFRSLYPSIIITHNVSPDTLNREGCKEYDVAPQVGHRFCKDFPGFIP

SLLGDLLEERQKIKKKMKATIDPIERKLLDYRQRAIKILANSYYGYYGYA

RARWYCKECAESVTAWGREYITMTIKEIEEKYGFKVIYSDTDGFFATIPG

ADAETVKKKAMEFLKYINAKLPGALELEYEGFYKRGFFVTKKKYAVIDEE

GKITTRGLEIVRRDWSEIAKETQARVLEALLKDGDVEKAVRIVKEVTEKL

SKYEVPPEKLVIHEQITRDLKDYKATGPHVAVAKRLAARGVKIRPGTVIS

YIVLKGSGRIGDRAIPFDEFDPTKHKYDAEYYIENQVLPAVERILRAFGY

RKEDLRYAKTRQVGLSAWLKPKGT.

III. Methods of Use of the Enzymes

Once an enzyme with desired characteristic(s) has been identified, the enzyme may be utilized in a variety of applications for polymerase activity that requires or may require reverse transcriptase activity. In some cases, the enzymes of the embodiments are used in situations where standard reverse transcriptases are employed, including at least next generation sequencing applications (applications with the ability to process millions of sequence reads in parallel, such as ILLUMINA® (Solexa) sequencing; Roche 454 sequencing; Ion torrent: Proton/PGM sequencing; Pacbio SMRT sequencing, and SOLiD sequencing). The enzyme(s) may be employed particularly when high fidelity is necessary or could be necessary. In this case, polymerase enzymes with proofreading exonuclease activity would be preferred. In certain embodiments, the enzymes are employed at least for molecular biology applications such as diagnostics (such as analyzing nucleic acids from a biological sample or derived from nucleic acids from a biological sample); cDNA library cloning, and next-generation RNA sequencing.

In certain embodiments, one can utilize one or more enzymes of the disclosure for direct RNA sequencing in the absence of first generating a cDNA intermediate. Such methods for the disclosure for applying the enzyme(s) (and others) allow beneficial avoidance of bias in generation of cDNA populations and subsequent amplification. In certain embodiments, enzymes of the disclosure have the ability to perform directional RNA sequencing, which preserves information about strand orientation, such as by the incorporation of dUTP into the first or second strand synthesis. Furthermore, in some aspects, enzymes of the embodiments can be used for both reverse transcription and subsequent amplification cDNA by polymerase chain reaction. Thus, in some aspects, reverse transcription-PCR can be performed in a single reaction using the same polymerase enzyme.

Further methods that can preferably employ an enzyme of the embodiments include, without limitation:

Method that require thermal denaturation of components, such as PCR inhibitors (e.g., proteins or heat sensitive molecules), prior to reverse transcription.

Improved reverse transcriptase and/or polymerization of nucleic acid species in compartments, such as water-in-oil emulsions. Such methods could be used to amplify, including pairing two or more RNA sequences with overlap extension RT-PCR, sequences from samples including individual cells or tissue samples. For example, these amplifications may include techniques such as digital droplet PCR.

The 3'-5' exonuclease activity of polymerases of the embodiments (e.g., CORE3) can be used to detect single nucleotide polymorphisms (SNPs) present in RNA or DNA sequences using a primer mismatch extension assay. These amplification products can be read out using sequencing and/or direct visualization.

Polymerase blends using polymerases of the embodiments (e.g., CORE3) with other known RTs (MMLV, AMV, Tth, and other engineered variants such as Taq polymerase) may provide further increased performance for the detection of difficult to synthesize nucleic acid sequences.

Polymerases of the embodiments have been demonstrated to work with multiple template compositions (DNA, RNA, and 2'C-Omethyl) and should reverse transcribe additional unnatural nucleic acid compositions, which could be applied to additional therapeutic, diagnostic, or sequencing applications.

Polymerases of the embodiments may be utilized in amplification schemes where the polymerase serves as a reverse transcriptase and other polymerases including DNA/RNA polymerases aid in amplification, such as: RT-Lamp, 3SR (NASBA), transcription mediated amplification (TMA), RCA, RPA, HDA, Strand displacement amplification.

Molecular cloning methods can also utilize polymerases of the embodiments such as SLIC, or Gibson assembly such that RNAs can directly be used or RNA containing primers.

Polymerases can be used for high fidelity cDNA library generation

Immuno-PCR amplification techniques can employ polymerases of the embodiments to detect small molecule or protein metabolites.

Polymerases of the embodiments can likewise be used for the in vitro or in vivo selection of RNA aptamer sequences including RNA-modified aptamers.

In vivo expression of polymerases of the embodiments can be used to convert RNA in cells into DNA. This could be used for, for instance for, programmed recombination (e.g., retrons, retroelements) or storage of nucleic acid information.

Polymerases can also be used in selection techniques for directed evolution including compartmentalized partnered replication or cooperative-CSR directed evolution techniques.

IV. Kits of the Disclosure

All or some of the essential materials and reagents required for producing, testing, and/or using enzymes of the disclosure may be provided in a kit. The kit may comprise one or more of RNA base-comprising primers, vectors, polymerase-encoding nucleic acids, buffers, ribonucleotides, deoxyribonucleotides, salts, and so forth corresponding to at least some embodiments of the enzyme production, characterization, and/or use. Embodiments of kits may comprise reagents for the detection and/or use of a control nucleic acid or enzyme, for example. Kits may provide instructions, controls, reagents, containers, and/or other materials for performing various assays or other methods (e.g., those described herein) using the enzymes of the disclosure.

The kits generally may comprise, in suitable means, distinct containers for each individual reagent, primer, and/or enzyme. In specific embodiments, the kit further comprises instructions for producing, testing, and/or using enzymes of the disclosure.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Strategies have been developed to allow directed evolution of polymerases in a high throughput manner, which have successfully led to polymerases with altered specificity and attributes (Pinheiro et al., 2012; Ghadessy et al., 2001). In the present disclosure, there was adaptation of the directed evolution framework to allow evolution of alternative bases or sugars in the template strand, a strategy called reverse transcription compartmentalized self-replication (RT-CSR) (FIG. 1B). Briefly, libraries of polymerase mutants are expressed in *E. coli* and subsequently subjected to emulsion PCR, physically separating cells into individual compartments and enabling the amplification of encoded polymerase inside the bacterium. The primers flanking the polymerase in the emulsion PCR are designed with RNA bases separating a capture sequence and a plasmid binding sequence. Upon second strand synthesis, the polymerases are challenged with RNA template derived from the initial elongated primer. The number of intervening RNA bases was increased to increase the stringency, allowing incrementally more challenging templates as the polymerases evolved (Table 1).

TABLE 1

RTCSR selection parameters used during the evolution of polB reverse transcriptases. The number of RNA bases in the RTCSR are denoted in the forward and reverse primers.

| Round # | Mutagenesis | RTCSR Primers | Total RNA | Plasmid Backbone | Induction aTc [ng/ml] |
|---|---|---|---|---|---|
| | | Initial Library | | | |
| 0 | error prone | | | colE1 (-rop) | |
| 1 | error prone | RTCSR.F/RTCSR.R | 0 | colE1 (-rop) | 200 |
| 2 | error prone | RTCSR.F/RTCSR.R | 0 | colE1 (-rop) | 200 |
| 3 | N/A | RTCSR.F/RTCSR.R | 0 | colE1 (-rop) | 200 |
| 4 | N/A | RTCSR.RNA5.F/RTCSR.RNA5.R | 10 | colE1 (-rop) | 200 |
| 5 | error prone | RTCSR.RNA5.F/RTCSR.RNA5.R | 10 | colE1 (-rop) | 200 |
| 6 | N/A | RTCSR.RNA5.F/RTCSR.RNA5.R | 10 | colE1 (-rop) | 200 |
| 7 | error prone | RTCSR.RNA10.F/RTCSR.RNA5.R | 15 | colE1 (-rop) | 200 |
| 8 | N/A | RICSR.RNA10.F/RTCSR.RNA5.R | 15 | colE1 (-rop) | 200 |
| | | KOD97 Library | | | |
| 0 | error prone (R97 NNS) | | | colE1 (-rop) | |
| 1 | N/A | RTCSR.RNA5.F/RTCSR.RNA5.R | 10 | colE1 (-rop) | 200 |
| 2 | error prone | RTCSR.RNA5.F/RTCSR.RNA5.R | 10 | colE1 (-rop) | 200 |
| 3 | N/A | RTCSR.RNA10.F/RTCSR.RNA5.R | 15 | colE1 (-rop) | 200 |
| 4 | error prone | RTCSR.RNA10.F/RTCSR.RNA5.R | 15 | colE1 (-rop) | 200 |
| 5 | N/A | RTCSR.RNA10.F2/RTCSR.RNA10.R2 | 20 | colE1 (-rop) | 200 |
| 6 | error prone | RTCSR.RNA10.F2/RTCSR.RNA10.R2 | 20 | colE1 (-rop) | 200 |
| 7 | N/A | RTCSR.RNA15.F2/RTCSR.RNA10.R2 | 25 | colE1 (-rop) | 200 |
| 8 | error prone | RTCSR.RNA15.F2/RTCSR.RNA10.R2 | 25 | colE1 (-rop) | 200 |
| 9 | N/A | RTCSR.RNA52.F2/RTCSR.RNA10.R2 | 62 | colE1 (-rop) | 200 |
| 10 | N/A | RTCSR.RNA52.F2/RTCSR.RNA10.R2 | 62 | colE1 (-rop) | 200 |
| 11 | N/A | RTCSR.RNA52.F2/RTCSR.RNA48.R3 | 100 | colE1 (-rop) | 200 |

TABLE 1-continued

RTCSR selection parameters used during the evolution of polB reverse transcriptases. The number of RNA bases in the RTCSR are denoted in the forward and reverse primers.

| Round # | Mutagenesis | RTCSR Primers | Total RNA | Plasmid Backbone | Induction aTc [ng/ml] |
|---|---|---|---|---|---|
| 12 | N/A | RTCSR.RNA52.F2/RTCSR.RNA48.R3 | 100 | colE1 (-rop) | 200 |
| 13 | N/A | RTCSR.RNA52.F2/RTCSR.RNA48.R3 | 100 | p15A | 20 |
| 14 | N/A | RTCSR.RNA52.F2/RTCSR.RNA48.R3 | 100 | p15A | 20 |
| 15 | N/A | RTCSR.RNA52.F2/RTCSR.RNA48.R3 | 100 | p15A | 20 |
| 16 | N/A | RTCSR.RNA52.F2/RTCSR.RNA48.R3 | 100 | p15A | 20 |
| 17 | N/A | RTCSR.RNA88.F2/RTCSR.RNA88.R3 | 176 | colE1 (-rop) | 200 |
| 18 | N/A | RTCSR.RNA88.F2/RTCSR.RNA88.R3 | 176 | colE1 (-rop) | 200 |

Evolution was initiated by evenly distributing mutations across the KOD polymerase by error prone PCR, as a targeted approach was deemed impractical due to extensive interactions between the polymerase and the template strand. Initially, a modest selection pressure was used, containing 10 total RNA bases (5 per each priming oligonucleotide), as this condition exceeded the number of template RNA bases wildtype KOD could polymerize. Upon sequencing the pool after eight rounds, mutations in position R97 were observed in over 90% of the variants. This general region of the polymerase is known to induce stalling at uracil residues (Killelea et al., 2010; Firbank et al., 2008), but unlike the more common mutation to inactivate this function (V93Q)(Fogg et al., 2002), analysis made during developments of embodiments herein reveals that R97 is positioned to recognize the T hydroxyl of template RNAs. A full randomization of this position was then made before continuing the selection.

Another eighteen rounds of selection were performed on the polymerase pool, introducing diversity as needed. The selection pressure was gradually increased until primers in the selection were completely composed of RNA, requiring reverse transcription to occur every thermal-cycle in order to maintain exponential amplification in the emulsion PCR. Deep sequencing of the polymerase pool identified crucial mutations for the adaptation of reverse transcriptase ability (FIG. 1C and Table 2).

TABLE 2

Deep sequencing of RTCSR libraries. Amino acid residues with mutations occurring in 10% of the population are shown in order of frequency. Some positions contained several amino acid possibilities. Synonymous mutations are not shown.

| Amino acid position | Mutation Frequency | Amino acid change | Variant Frequency |
|---|---|---|---|
| Initial Selection | | | |
| 97 | 94.2% | R → H | 58.70% |
|  |  | R → S | 22.30% |
|  |  | R → C | 13.20% |
| 587 | 27.9% | F → L | 15.10% |
|  |  | F → L | 12.80% |
| 119 |  | R → H | 10.90% |
| Round 10 | | | |
| 97 | 97.9% | R → F | 17.70% |
|  |  | R → A | 11.80% |
|  |  | Other | 68.40% |
| 384 |  | Y → H | 81.20% |
| 210 |  | N → D | 63.70% |
| 389 |  | V → I | 50.20% |
| 587 | 37.3% | F → I | 14.00% |
|  |  | F → L | 23.30% |
| 711 |  | G → S | 29.30% |
| 664 |  | E → K | 29.20% |
| 168 |  | A → T | 25.70% |
| 521 |  | I → L | 24.20% |
| 454 |  | G → D | 22.20% |
| 490 |  | A → T | 17.40% |
| 634 |  | G → D | 16.00% |
| 528 |  | I → L | 14.50% |
| 734 |  | E → K | 14.10% |
| 493 |  | Y → C | 13.90% |
| 311 |  | Y → C | 12.10% |
| 292 |  | A → T | 11.80% |
| 137 |  | M → I | 11.30% |
| 677 |  | G → S | 10.90% |
| 440 |  | R → H | 10.80% |
| 144 |  | T → A | 10.80% |
| 171 |  | I → V | 10.60% |
| 748 |  | F → Y | 10.00% |
| Round 18 | | | |
| 384 |  | Y → H | 96.00% |
| 97 | 93.3% | R → A | 20.80% |
|  |  | R → F | 18.00% |
|  |  | Other | 54.50% |
| 389 |  | V → I | 91.90% |
| 210 |  | N → D | 84.90% |
| 493 | 83.3% | Y → C | 59.00% |
|  |  | Y → L | 13.20% |
|  |  | Y → F | 11.10% |
| 664 | 82.7% | E → K | 60.40% |
|  |  | E → Q | 22.30% |
| 711 | 75.0% | G → S | 46.80% |
|  |  | G → V | 28.20% |
| 521 |  | I → L | 59.40% |
| 490 |  | A → T | 58.50% |
| 587 | 55.1% | F → L | 36.80% |
|  |  |  | 18.30% |
| 168 |  | A → T | 36.70% |
| 734 |  | E → K | 34.50% |
| 137 | 33.9% | M → I | 20.30% |
|  |  | M → L | 13.60% |
| 748 |  | F → Y | 22.40% |
| 735 |  | N → K | 18.80% |
| 593 |  | K → N | 16.90% |
| 590 |  | T → A | 15.80% |
| 605 |  | T → I | 13.20% |
| 143 |  | E → G | 13.00% |
| 501 |  | R → H | 12.90% |
| 144 |  | T → A | 12.50% |

TABLE 2-continued

Deep sequencing of RTCSR libraries. Amino acid residues with mutations occurring in 10% of the population are shown in order of frequency. Some positions contained several amino acid possibilities. Synonymous mutations are not shown.

| Amino acid position | Mutation Frequency | Amino acid change | Variant Frequency |
|---|---|---|---|
| 150 | | E → D | 12.20% |
| 145 | | L → P | 11.50% |
| 741 | | V → A | 11.30% |
| 692 | | K → R | 11.20% |
| 454 | | G → D | 11.10% |

The majority of conserved mutations directly interact with the template strand, are secondary shell interactions, or are known to inactivate the proofreading activity (N210D). These mutations span the length of the template recognition interface, being situated in the regions recognizing the incoming template (R97), the active site (Y384), or post polymerization—the nascent RNA/DNA duplex (V389, I521, E664, G711)(Bergen et al., 2013).

Figure 4:
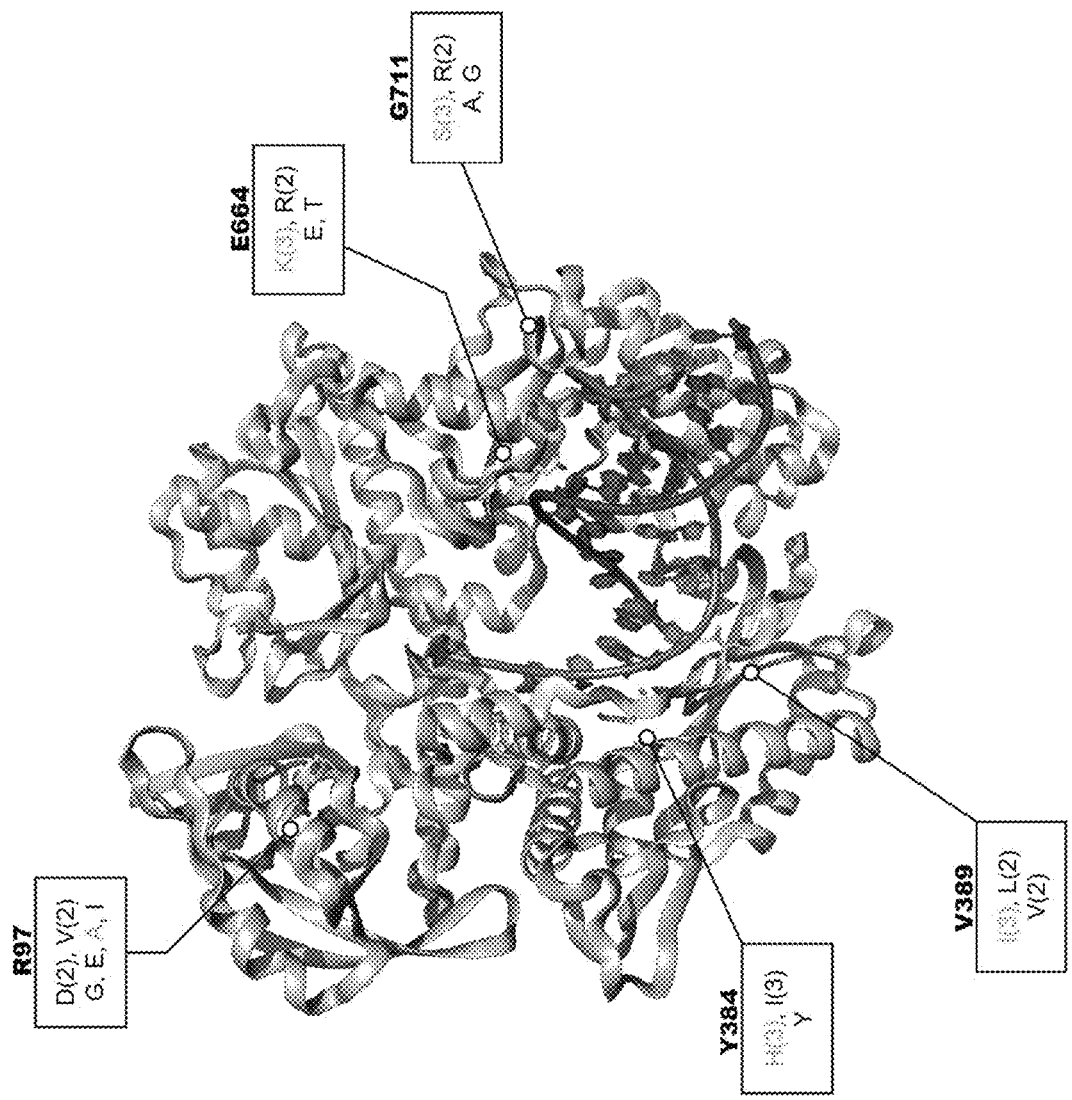
FIG. 4 shows that five residues (R97, Y384, V389, E664, and G711) were fully randomized by NNS mutagenesis. Three rounds of RTCSR were performed and clones were sequenced. The mutations were counted from the sequencing and labeled on the structure. Residues found in the initial selection are labeled in green. Figure adapted from PDB 4K8Z.

Based on the single directed evolution experiment, it was unclear whether the conserved mutations served to abolish strict DNA specificity or promoted RNA specificity. In attempt to answer this question, the RTCSR process was replayed but this time fully randomizing suspected key residues in the parental polymerase. This revealed a potentially two-pronged evolutionary process, the loss of function at certain positions (e.g., R97) based on many viable solutions and mutations potentially promoting RNA utilization (e.g. Y384H, E664K) due to evolutionary amino acid preferences (FIG. 4). In the contextual view of the wildtype polymerase, the observation that (1) many mutations were required for efficient reverse transcription ability and (2) the mutations were spread across the entire template interface, suggests that the wild-type polymerase utilizes a series of checkpoints to discriminate DNA from RNA: as the template enters the enzyme, as polymerization occurs at the active site, and at the nascent duplex.

Figure 5:
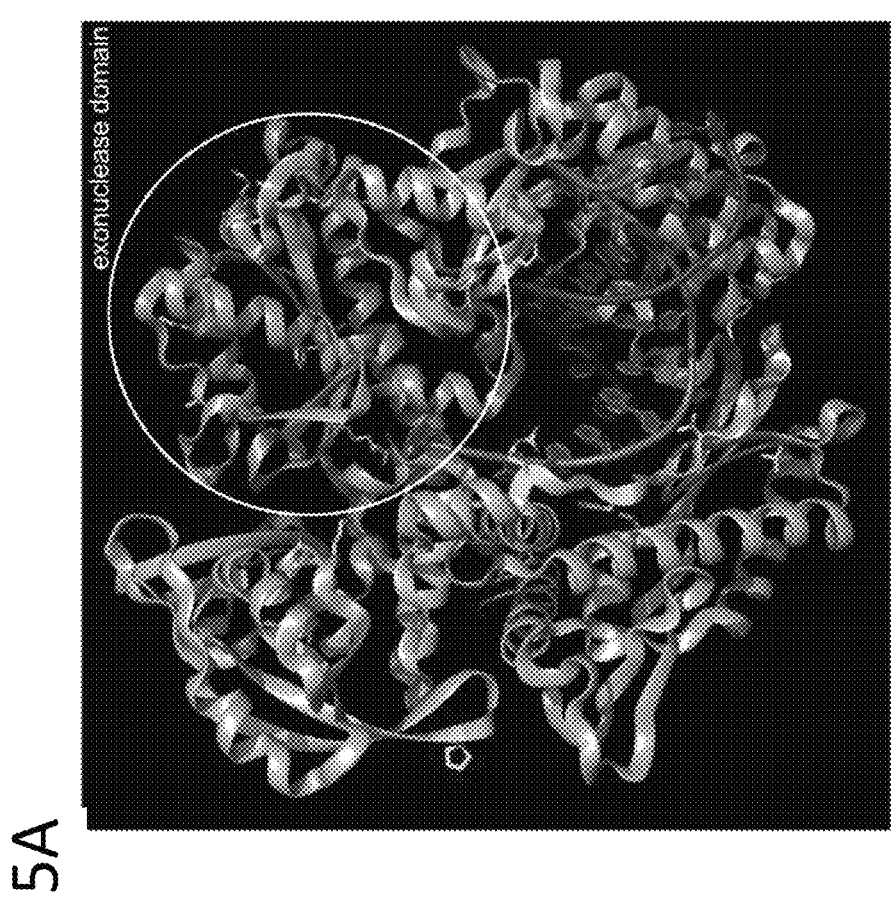
FIGS. 5A-5C. 5A, Mutations in the B11 polymerase (yellow) are mapped onto the KOD polymerase (grey with DNA primer:template duplex in blue). Thirty seven mutations were accumulated, many found in the exonuclease. 5B, Examination of the active site of the B11 polymerase shows a mutation at glutamate 143 to glycine (SEQ ID NO. 4 and 5). 5C, Functional assays reveal B11 polymerase is capable of single enzyme RTPCR of a 500 base pair region of the HSPCB gene, as well as the B11 with grafted wildtype proofreading domain. Proofreading activity was qualitatively measured in a dideoxy-mismatch PCR, which requires removal of a 3' deoxy mismatch primer before polymerization occurs.

Screening the pool for active polymerases yielded a variant, B11, with 37 mutations. The polymerase was found to be capable of reverse transcription of at least 500 base pairs. Sequencing revealed that the polymerase had inactivated the proofreading domain, which was confirmed in functional assays (FIG. 5). It was considered that transplantation of the wildtype proofreading domain might restore this activity. The hybrid recovered activity, but to barely detectable levels. Despite the proofreading domain regaining activity, the RT activity in the B11 polymerase was still robust, indicating that RT activity is compatible with 3'-5' exonuclease activity. Encouraged by these results, several designed polymerases were constructed to minimize what were likely extraneous mutations likely introduced in the RTCSR process, in certain aspects.

Figure 6:
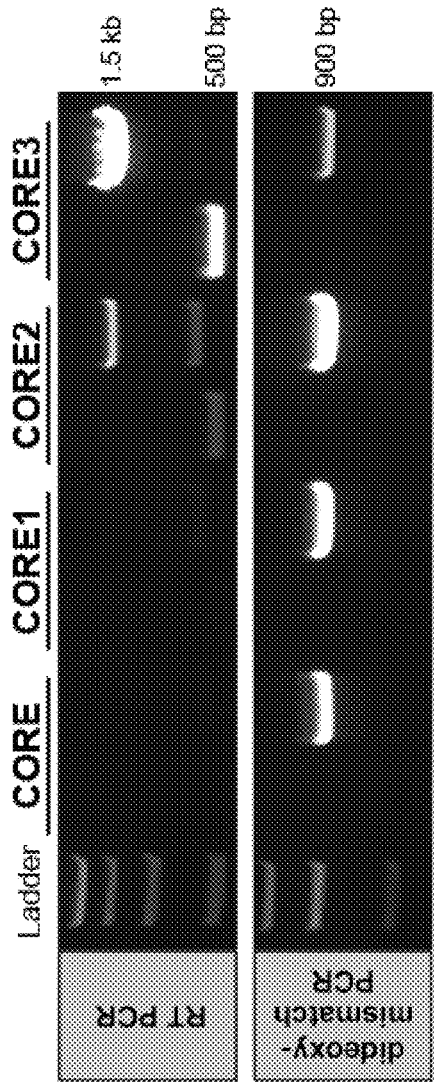
FIG. 6. The designed polymerases based on the B11 scaffold and deep sequencing information were constructed and tested in an RTPCR assay (HSPCB) and proofreading assay. The mutations introduced into the wildtype KOD polymerase are shown for each of the designed reverse transcriptases.

Polymerases were designed based on the B11 scaffold, as well as sequencing data of the pool. A series of polymerases were built around what were likely a core set of mutations, as identified by highly conserved mutations and residues in proximity to the template. Testing revealed that each of the polymerases were active but reverse transcriptase activity was enhanced upon additional mutations (FIG. 6). Proofreading activity was demonstrated in each of the core polymerase designs—indicating that constructing more wildtype-like polymerases did enhanced proofreading. Based on activity of these polymerases, the CORE3 polymerase was chosen to characterize further, as it has the most substantial reverse transcriptase activity while still maintaining its proofreading capability.

Figure 7:
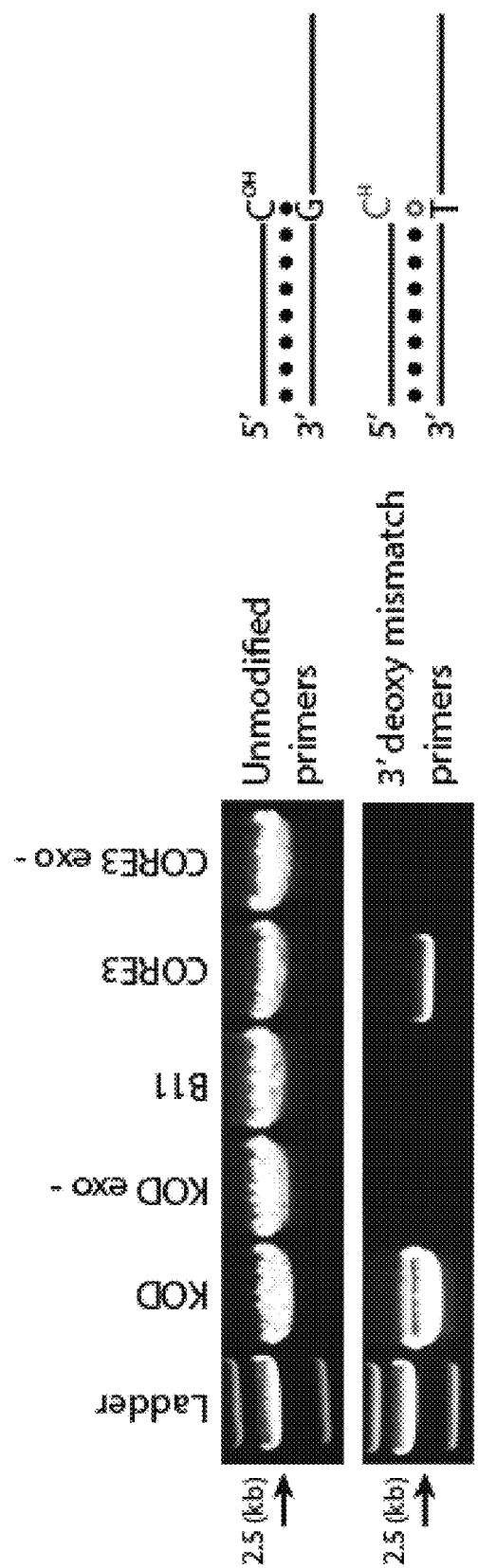
FIG. 7. To assess the DNA polymerization, a PCR was performed using unmodified primers on a 2.5 kilobase fragment. Proofreading (3'-5' exonuclease activity) was tested by the addition of 3' deoxy mismatch primers into the PCR. Only polymerases capable of removing the mismatch can extend the primer and perform PCR.

Based on the screening metric, the CORE3 polymerase had proofreading activity on DNA templates (FIG. 7) but it was unclear whether the proofreading mechanism could occur during reverse transcription, as RNA:DNA duplexes adopt alternative conformations not found in DNA-only duplexes (Wang et al., 1982). To address this, oligonucleotides were synthesized so that the 3' end would either form a canonical 3' hydroxyl matched base pair or a 3' deoxy mismatched pair—analogous a newly mis-incorporated nucleotide, which can stimulate proofreading activity. When primer extensions were performed using a DNA template, both parental KOD and CORE3 both were capable of extending the mismatched primer in a single extension, while their exonuclease deficient counterparts were not. Repeating this assay using an RNA template, the CORE3 polymerase did not lose proofreading activity and it was comparable to the proofreading activity while polymerizing on a DNA template (FIG. 2A).

Figure 8:
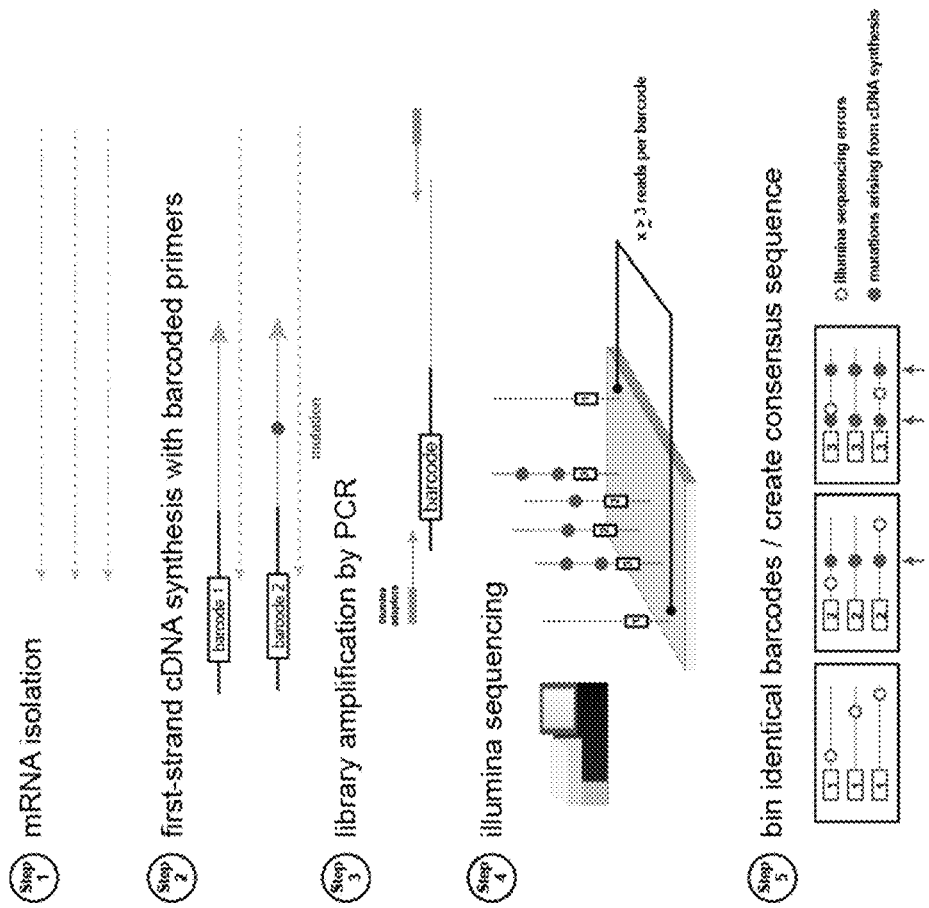
FIG. 8. The SSCS method for reverse transcription is outlined above. In step 1, total mRNA is isolated. Step 2, barcoded gene specific primers are used to perform first strand synthesis and cDNA is isolated. Step 3, the cDNAs are amplified with primers amplifying the cDNAs while preserving the barcodes. Step 4, ILLUMINA® MISEQ® 2x250 sequencer paired end reads are performed enabling multiple reads of the same initial cDNA. Step 5, identical barcodes are binned and used to create a consensus sequence. Only barcodes that were read over 3 times were used in the alignment, reducing sequencer mutations by >99%.

Given that CORE3 maintains proofreading during reverse transcription, the impact that proofreading could have on reverse transcription fidelity was considered. A strategy was devised based on recent advances that have significantly reduced ILLUMINA® sequencing errors by implementing barcodes into adaptors sequences (Schmitt et al., 2012), allowing for precise detection of errors unambiguously, unlike traditional genetic based assays. Unique barcodes were designed into reverse transcription primers of human HSPCB and PolR2A genes. After RT, a subsequent PCR of the cDNAs copies these barcodes, allowing multiple reads during deep sequencing (FIG. 8). Binning identical barcodes (N≥3) and creating consensus sequences reduces background errors by several orders of magnitude. Sequencing of the genes revealed the mutational spectra of MMLV, CORE3 and the proofreading deficient CORE3 (exo-) (FIG. 2B and Table 3).

TABLE 3 a, Fidelity profile for reverse transcription on two human genes, HSPCB and PolR2A using the SSCS technique. The error rate is calculated by dividing total mutations (mismatch + indel) over the total number of bases sequenced. The frequency of each possible mutation is listed as a percentage of total mutations. b, Fidelity profile for DNA template (cloned plasmid DNA) polymerization using cloned HSPCB.

| Polymerase | CORE3 | MMLV | CORE3 exo- | B11 | KOD |
|---|---|---|---|---|---|
| | | | a | | |
| | | HSPCB reverse transcription | | | |
| Total Matches | 1.44E+07 | 1.20E+06 | 1.10E+06 | 1.33E+07 | |
| Total Mismatch | 520 | 124 | 102 | 3136 | |

TABLE 3-continued a, Fidelity profile for reverse transcription on two human genes, HSPCB and PolR2A using the SSCS technique. The error rate is calculated by dividing total mutations (mismatch + indel) over the total number of bases sequenced. The frequency of each possible mutation is listed as a percentage of total mutations. b, Fidelity profile for DNA template (cloned plasmid DNA) polymerization using cloned HSPCB.

| Polymerase | CORE3 | MMLV | CORE3 exo- | B11 | KOD |
|---|---|---|---|---|---|
| Total Indel | 15 | 7 | 11 | 416 | |
| Error Rate | 3.71E−05 | 1.10E−04 | 1.03E−04 | 2.66E−04 | |
| Base: Mutation | | Mutation Frequency | | | |
| T to A | 1.92% | 2.42% | 20.59% | 23.82% | |
| G to A | 27.69% | 29.03% | 13.73% | 612% | |
| T to C | 5.58% | 22.58% | 1.96% | 2.68% | |
| G to C | 0.38% | 0.00% | 0.00% | 0.00% | |
| T to G | 3.27% | 0.00% | 6.86% | 8.16% | |
| C to G | 0.38% | 0.81% | 0.98% | 2.36% | |
| C to A | 3.46% | 3.23% | 10.78% | 6.92% | |
| A to T | 1.54% | 9.68% | 0.98% | 1.66% | |
| G to T | 31.73% | 1.61% | 0.98% | 4.11% | |
| C to T | 11.35% | 13.71% | 11.76% | 10.01% | |
| A to C | 0.19% | 8.06% | 0.98% | 0.70% | |
| A to G | 12.50% | 8.87% | 30.39% | 33.45% | |
| | | PolR2A reverse transcription | | | |
| Total Matches | 1.66E+07 | 1.12E+06 | 1.26E+07 | | |
| Total Mismatch | 537 | 536 | 4175 | | |
| Total Indel | 54 | 7 | 965 | | |
| Error Rate | 3.56E−05 | 4.86E−04 | 4.08E−04 | | |
| Base: Mutation | | Mutation Frequency | | | |
| T to A | 2.61% | 0.56% | 35.52% | | |
| G to A | 14.34% | 1.68% | 2.18% | | |
| T to C | 13.04% | 88.25% | 2.68% | | |
| O to C | 0.74% | 0.37% | 0.05% | | |
| T to G | 1.49% | 0.00% | 1.51% | | |
| C to G | 0.37% | 0.19% | 2.35% | | |
| C to A | 6.89% | 0.00% | 5.27% | | |
| A to T | 1.12% | 0.19% | 2.75% | | |
| G to T | 34.08% | 2.05% | 3.83% | | |
| C to T | 12.66% | 2.80% | 8.02% | | |
| A to C | 0.56% | 0.75% | 1.20% | | |
| A to G | 12.10% | 3.17% | 34.63% | | |
| | | b HSPCB (DNA Template) | | | |
| Total Matches | 1.84E+07 | 2.23E+06 | 4.65E+06 | 2.33E+07 | 1.49E+07 |
| Total Mismatch | 1521 | 297 | 795 | 5697 | 627 |
| Total Indel | 305 | 17 | 92 | 852 | 5 |
| Error Rate | 9.93E−05 | 1.41E−04 | 1.91E−04 | 2.80E−04 | 4.23E−05 |
| Base: Mutation | | Mutation Frequency | | | |
| T to A | 4.67% | 5.39% | 15.47% | 19.89% | 2.71% |
| G to A | 13.41% | 14.14% | 14.97% | 9.60% | 26.16% |
| T to C | 3.35% | 7.74% | 3.40% | 3.48% | 5.74% |
| G to C | 0.13% | 0.34% | 1.13% | 2.42% | 0.00% |
| T to G | 0.66% | 0.34% | 2.14% | 3.39% | 0.00% |
| C to G | 5.85% | 1.35% | 11.45% | 11.01% | 0.32% |
| C to A | 14.73% | 10.10% | 16.48% | 10.88% | 34.13% |
| A to T | 1.58% | 12.46% | 2.52% | 6.90% | 0.48% |
| G to T | 6.38% | 7.41% | 2.64% | 2.98% | 6.54% |
| C to T | 12.29% | 8.08% | 9.06% | 10.67% | 8.29% |
| A to C | 0.72% | 12.79% | 0.75% | 1.79% | 0.80% |
| A to G | 36.23% | 19.87% | 20.00% | 16.99% | 14.83% |

The MMLV control enzyme had an error rate of $1.1 \times 10$ while the CORE3 enzyme had an error of $3.71 \times 10^{-5}$ (~3-fold improvement). Inactivating the proofreading of CORE3 lowers the observed fidelity nearly 3 fold—further supporting that CORE3 contains active proofreading while reverse transcribing. In specific embodiments, the true error rate for CORE3 is lower given that the SSCS technique has a lower limit of detection nearly identical to the error rate observed for CORE3—due to artifacts, which was confirmed by experiments measuring wild-type KOD on DNA (Table 3)(Schmitt et al., 2012). In addition, transcriptionally derived errors are unaccounted for and other experiments have demonstrated that an active proofreading domain can increase fidelity ~30-fold (Nishioka et al., 2001).

Figure 3:
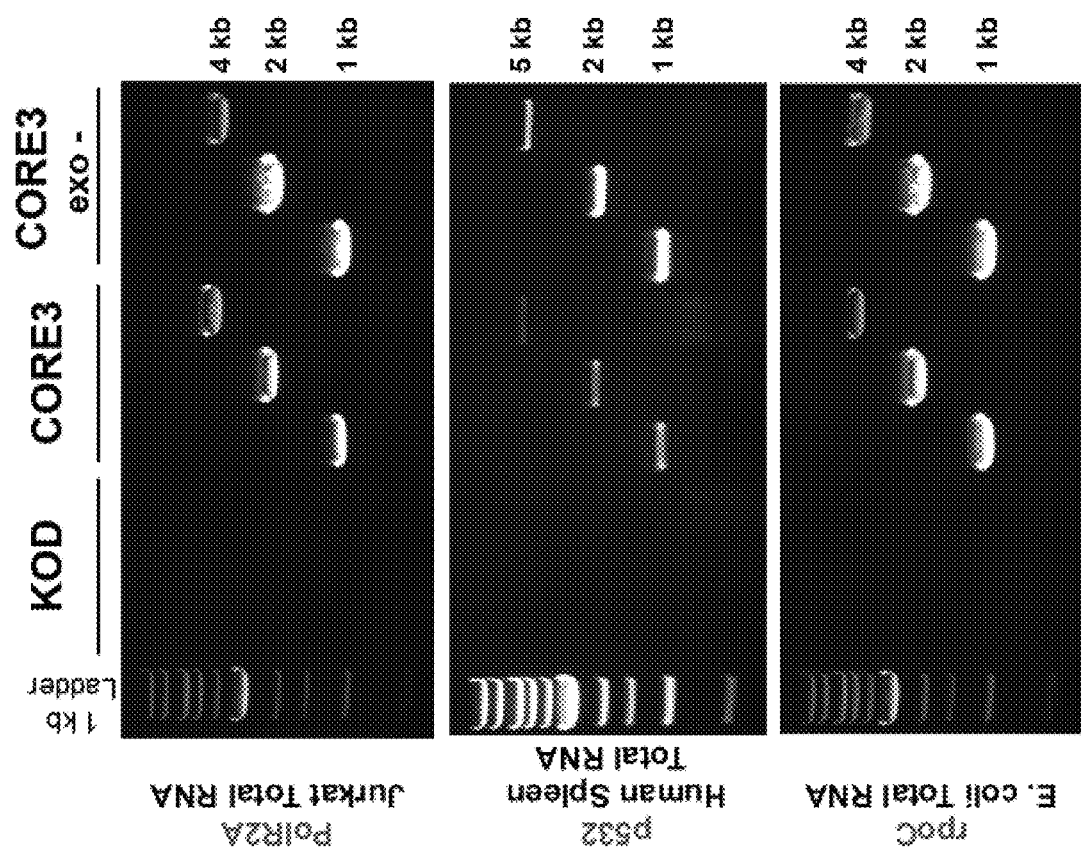
FIG. 3 demonstrates single enzyme RTPCR on various genes and RNA samples. Reverse transcription PCR (RT-PCR) was performed using KOD polymerase, CORE3, and the proofreading deficient version of CORE3 (exo-). Various genes were amplified, two human genes, Po1R2A and p532, and rpoC from E. coli. Using a gene specific forward and reverse primers, various size amplicons were amplified from these genes, demonstrating efficient single enzyme RTPCR.

Having seen robust reverse transcription with shorter templates, the CORE3 polymerase was tested in a single enzyme RT-PCR (in which the CORE3 polymerase performs both the first-strand reverse transcription as well as the PCR amplification) for much longer templates. Several independent RNA sources and gene loci were chosen to mitigate the possibility of contaminating DNA. Eukaryotic mRNAs were emphasized in the testing, as DNA contamination would create a unique size profile, due retention of introns. Across three unique RNA samples and genes, the CORE3 polymerase was highly capable of single enzyme RTPCR, successfully generating amplicons larger than 5 kilobases (FIG. 3). The experiments indicate that inactivating the proofreading of CORE3 (N210D mutation), which generally increases product yield, was not necessary to achieve these large amplicons.

Figure 9:
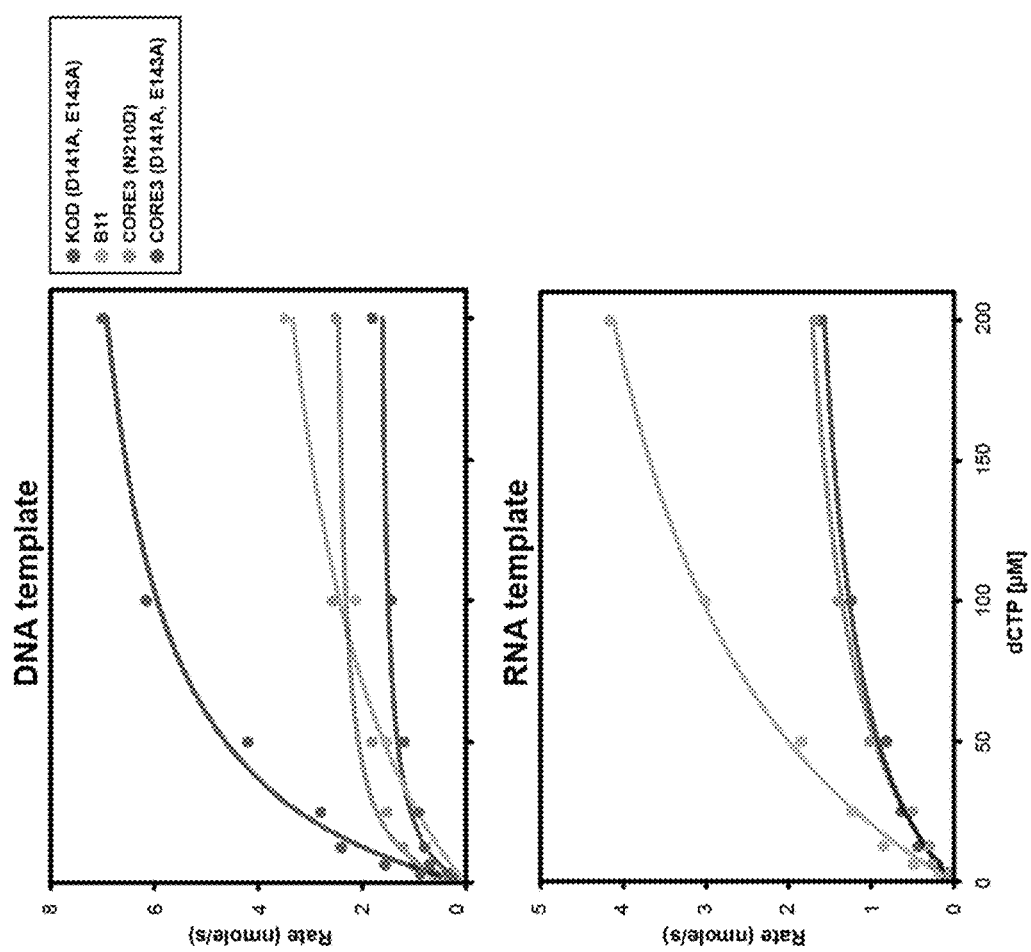
FIG. 9. Steady-state kinetics of polymerase variants. Initial rates of single nucleotide (dCTP) incorporation by exonuclease deficient polymerases were plotted against the concentration of dCTP using DNA or RNA templates. Kinetic parameters were estimated by fitting the data to the Michaelis-Menten equation. KOD was able to incorporate dCTP on DNA:RNA duplexes. However, the data could not be fit.

Having shown that the CORE3 polymerase is capable of reverse transcribing long RNAs with proofreading ability, it was considered how the evolutionary process enabled such a radical shift in function. Steady state analysis of incorporation of radio-labeled dCTP of the ancestral and evolved polymerases reveals a dramatically decreased $K_m$ on RNA, from nondetectable substrate binding (in the parental KOD enzyme) to affinities comparable to wild-type KOD binding on a DNA template (Table 4 and FIG. 9).

TABLE 4

Steady state kinetics for polymerase variants on DNA and RNA templates. (n.d. was not determined due to inactivity)

| Enzyme | DNA | | | RNA | | |
|---|---|---|---|---|---|---|
| | kcat | Km | kcat/Km | kcat | Km | kcat/Km |
| KOD | 160.4 | 39.7 | 4.0 | n.d. | n. d. | nd. |
| B11 | 48.2 | 7.9 | 6.1 | 54.5 | 23.1 | 2.4 |
| CORE3 | 49.1 | 15.7 | 3.1 | 52.3 | 51.5 | 1.0 |
| CORE3 exo- | 56.8 | 12.1 | 4.7 | 55.2 | 31.1 | 1.8 |

The $K_m$ of the evolved polymerases appeared to be lowered for DNA templates as well, which is a general phenomenon while evolving DNA polymerases using CSR (data not shown), presumably to increase product yield in the emulsion PCR reaction. While the exact role of each mutation in CORE3 is not known, the increased affinity is in part due to the E664K mutation which was observed in high frequency throughout the evolution experiment, and has been demonstrated to greatly increase binding DNA/RNA heteroduplexes (Cozens et al., 2012).

Figures 10A, 10B:
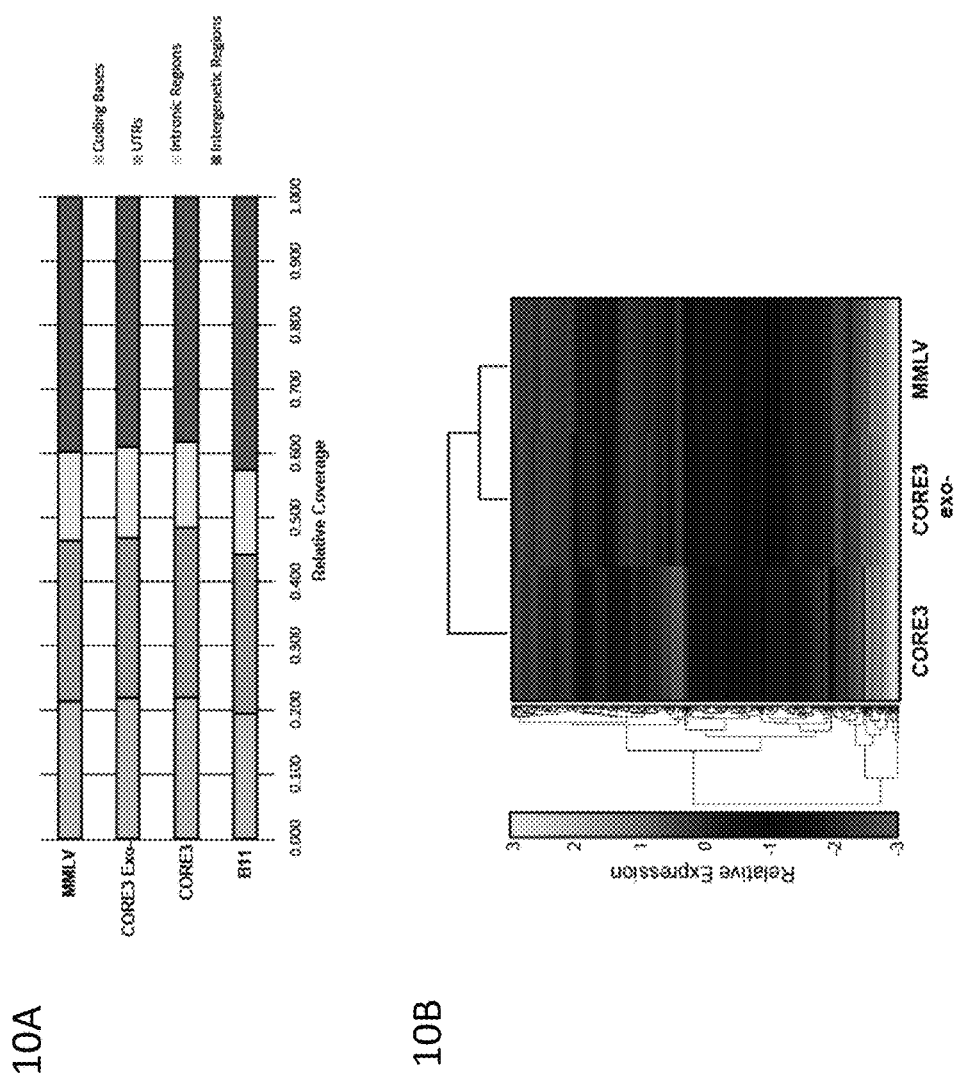
FIGS. 10A-10B. 10A, Relative coverage for various intracellular RNAs from gliobastoma cells for each reverse transcriptase. 10B, Clustergram of relative expression for the top 500 most expressed RNAs for MMLV, CORE3, and CORE3 (exo-).

The advantages of a high fidelity RT has great potential to increase understanding of transcriptomics, reducing biases and errors introduced in the reverse transcription step of next-gen RNA-Seq. To demonstrate the immediate utility, the CORE3 polymerase was implemented into a commonly used work flow for directional RNA sequencing (NEB-NEXT® library prep). The workflow was unaltered except the buffer and polymerase were changed to CORE3 in the reverse transcription step. Analysis revealed nearly identical coverage and expression profiles (FIG. 10), indicating that the proofreading activity of CORE3 does not introduce systematic biases of mRNA expression levels.

Figure 11:
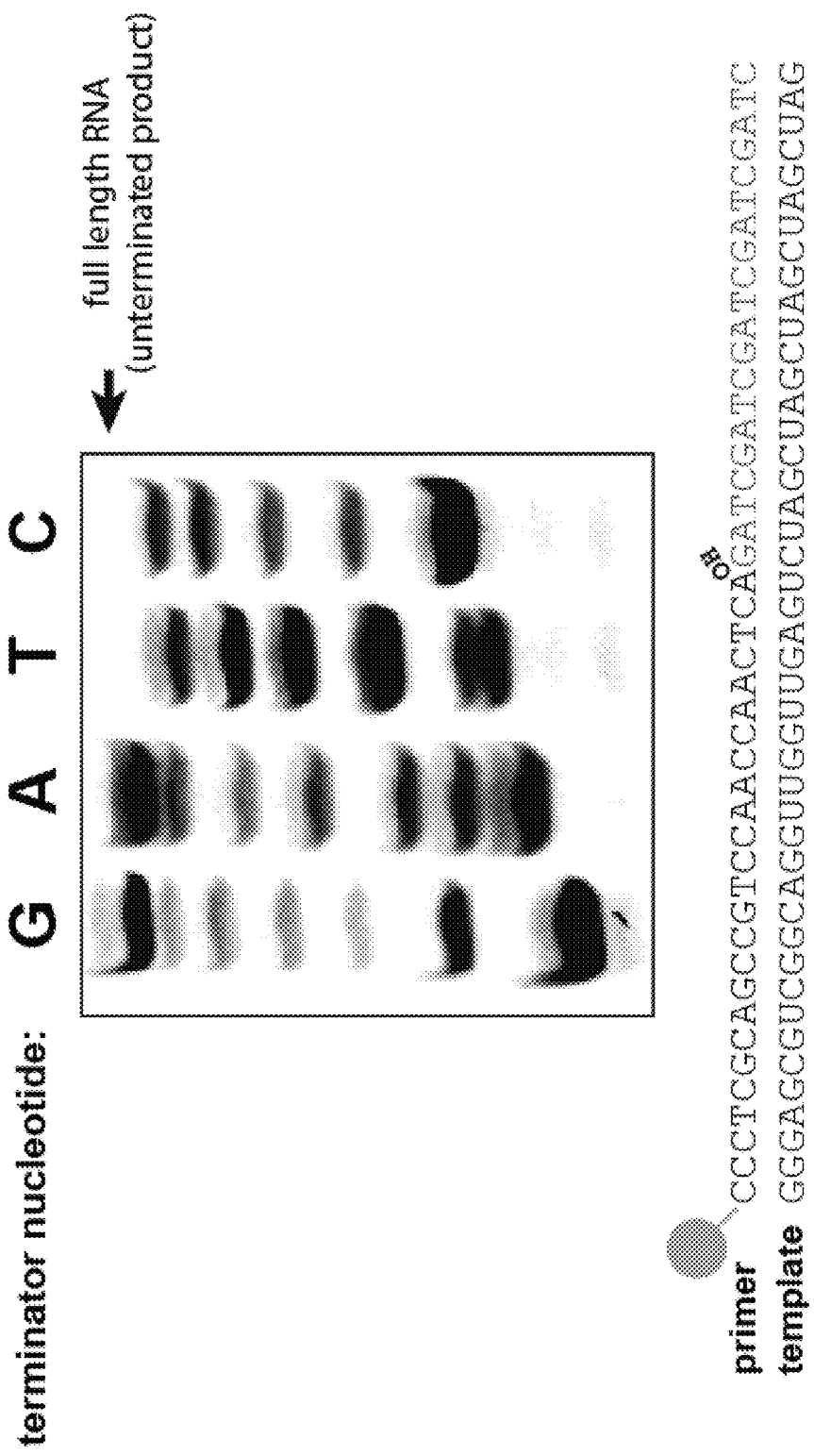
FIG. 11. Primer extension reactions were carried out with a 5' FAM labeled oligonucleotide with terminator nucleotides (ddGTP, ddATP, ddTTP, ddCTP) at a 25:1 ratio (ddXTP:dXTP). Reactions were performed with CORE3 exo- to prevent exonuclease cleavage of terminated extension products. The primer:template RNA complex is depicted with the 3' hydroxyl group on the labeled primer (SEQ ID NOS. 6 and 7). Termination region (sequenced bases) is shown in red.

Using the CORE3 polymerase, it was considered that it might be possible to bypass the need to create cDNA libraries all together, in specific embodiments. The process of cDNA synthesis and PCR amplification has long been known to introduce many biases through amplification (Hansen et al., 2010; Aird et al., 2011). CORE3 was utilized to directly sequence RNA using traditional Sanger sequencing approach. Single dideoxy-terminator nucleotides were mixed with normal dNTPs, such that termination would occur partially at each corresponding base, which could then be run on a sequencing gel or capillary. As a proof of concept, 20 nucleotides of a $GATC_5$ RNA repeat were sequenced (FIG. 11). Termination was apparent at each of the corresponding positions and the sequence could be determined. Given the constraints of Sanger sequencing, the proofreading version of CORE3 could not be used, however, direct RNA sequencing should be adaptable to single molecule sequencing platforms (such as Pacbio's SMRT sequencing system), allowing proofreading of the RNA and eliminating the biases created in cDNA synthesis and subsequent amplification.

By utilizing the RTCSR approach, an archaeal Family-B polymerase was morphed into a reverse transcriptase—establishing a family of reverse transcriptases entirely unbranched from natural RTs. The engineered polymerase can polymerize over long RNA templates with high accuracy and at elevated temperatures. High fidelity reverse transcription will enable more accurate understanding for many RNA processes. Mutations in RNA have been detected in many disease states, including cancer. The precise identification of rare somatic mutations in tissues are likely to drive a better understanding of the disease process and diagnostic tools. As RNA sequencing tools become more sophisticated, high fidelity reverse transcriptases will play a substantial role. The ability of the Family-B reverse transcriptase to perform RNA sequencing without the need to first create a cDNA library may become an invaluable tool for understanding the transcriptome at deeper levels.

The CORE3 polymerase reveals that high fidelity reverse transcription is possible, and further supports that low fidelity reverse transcription could be an adaptive aspect of retroviruses given that they have been shown to have enormous potential to evolve in response to selective pressures, such as the immune response (Wei et al., 1995). This is largely attributed to the vast diversity of the viral infection, forming what is often referred to as a quasispecies (Lauring et al., 2010; Eigen, 1971). This may confirm the notion that low fidelity reverse transcription is adaptive or maybe even essential for retroviral populations. The introduction of high fidelity reverse transcriptases into retroviruses, perhaps limiting the genetic diversity available by lowering mutation rates, may serve as a mechanism to make attenuated vaccines safer.

Example 2

Embodiment of Directed Evolution of Thermostable DNA Polymerases

The disclosure provides methods for producing derivative enzymes from a parent enzyme, wherein the derivative comprises one or more activities that is lacking in the parent enzyme. The methods may utilize steps that modify the parent enzyme by random means and/or by targeted means of modification. Embodiments of the disclosure include modifications to a parent DNA polymerase that lacked reverse transcriptase activity.

In specific embodiments, methods for generating enzyme derivatives employ a variation of the compartmentalized self-replication (CSR) method (Ghadessy et al. (2001); EP 1317539B). The CSR method is designed around the directed evolution of thermostable DNA polymerases. In CSR, primers are designed which flank the polymerase gene. Upon thermocycling (PCR), the polymerase enzyme will copy their own genes. In the present disclosure, the method was adapted to allow evolution of alternative bases or sugars in the template strand. Specifically, in the present variation of CSR, the primer design is modified from known CSR methods to enable the directed evolution of reverse transcriptases. The primers are designed such that a variable number of RNA bases are present in the primer. After the first cycle of PCR, the primers become templates for subsequent cycles. The method is designed such that only polymerases capable of reverse transcription are recovered. Increasing the number of RNA bases in the primer increase the stringency of reverse transcriptase activity. Primers can be composed entirely of RNA to allow maximum stringency (see FIG. 12).

Example 3

Exemplary Materials and Methods

The present example provides examples of materials and methods for embodiments of the disclosure.

Initial Reverse Transcription Test for Polymerases—

30 pmol of 5' fluorescein labeled primer (25FAM) were annealed with 30 pmol of template (TEMP.A.DNA/1RNA/5RNA) and 0.4 µg of polymerase by heat denaturation at 90° C. for 1 minute and allowing to cool to room temperature. Reactions were initiated by the addition of "start" mix which contained (50 mM Tris-HCl (pH8.4), 10 mM $(NH_4)_2SO_4$, 10 mM KCl, 2 mM $MgSO_4$ and 200 µM dNTPs. MMLV polymerase was treated according to manufacturer's recommendations (New England Biolabs). Reactions were incubated for 2 minutes at 68° C. until terminated by the addition of EDTA to a final concentration of 25 mM. The labeled primer was removed from the template strand by heating sample at 75° C. for 5 minutes in 1× dye (47.5% formamide, 0.01% SDS) and 1 nmol of unlabeled BLOCKER oligonucleotide (to competitively bind the template strand). Samples were run on a 20% (7 M urea) acrylamide gel.

Reverse Transcription CSR (RTCSR)—

KOD polymerase libraries were created through error prone PCR unless otherwise indicated to have a mutation rate of ~1-2 amino acid mutations per gene. Libraries were cloned into tetracycline inducible vector and electroporated into DH10B *E. coli*. Library sizes were maintained with a transformation efficiency of at least $10^6$, but more typically $10^7$-$10^8$. Overnight library cultures were seeded at a 1:20 ratio into fresh 2×YT media supplemented with 100 µg/mL ampicillin and grown for 1 hour at 37° C. Cells were subsequently induced by the addition of anhydrotetracycline (typically at a final concentration of 200 ng/mL) and incubated at 37° C. for 4 hours. Induced cells (200 µL total) were spun in a tabletop centrifuge at 3,000×g for 8 minutes. The supernatant was discarded and the cell pellet was resuspended in RTCSR mix: 1× Selection buffer (50 mM Tris-HCl (pH8.4), 10 mM $(NH_4)_2SO_4$, 10 mM KCl, 2 mM $MgSO_4$), 260 µM dNTPs, 530 nM forward and reverse RNA containing primers (detailed in Supplementary Table 1). The resuspended cells were placed into a 2 mL tube with a 1 mL rubber syringe plunger and 600 µL of oil mix (73% Tegosoft DEC, 7% AbilWE09 (Evonik), and 20% mineral oil (Sigma-Aldrich)). The emulsion was created by placing the cell and oil mix on a TissueLyser LT (Qiagen) with a program of 42 Hz for 4 minutes. The emulsified cells were thermal-cycled with the program: 95° C.-3 min, 20× (95° C.—30 sec, 62° C.—30 sec, 68° C.—2 min). Emulsions were broken by spinning the reaction (10,000×g—5 min), removing the top oil phase, adding 150 µL of $H_2O$ and 750 µL chloroform, vortexing vigorously, and finally phase separating in a phase lock tube (5 Prime). The aqueous phase was cleaned using a PCR purification column which results in purified DNA, including PCR products as well as plasmid DNA. Subamplification with corresponding outnested recovery primers ensures that only polymerases that reverse transcribed are PCR amplified. Typically this is achieved by addition of 1/10 the total purified emulsion using Accuprime Pfx (ThermoFisher) in a 20 cycle PCR, however challenging rounds of selection could require increasing the input DNA or cycle number to achieve desired amplification.

Cloning and Purification of Polymerase Variants—

*Escherichia coli* DH10B and BL21 (DE3) strains were used for cloning and expression, respectively. Strains were maintained on either Superior or 2×YT growth media. Polymerases were cloned into a modified pET21 vector using NdeI and BamHI sites. Overnight cultures of BL21 (DE3) harboring each of the variants were grown overnight in Superior broth at 37° C. Cells were then diluted 1:250, and protein production was induced with 1 mM IPTG during mid-log at 18° C. for 20 hrs. Harvested cells were flash-frozen and lysed by sonication in 10 mM phosphate, 100 mM NaCl, 0.1 mM EDTA, 1 mM DTT, 10% glycerol, pH 7 (Buffer A). Cleared cell lysates were heated at 85° C. for 25 min, cooled on ice for 20 minutes, and filtered (0.2 µm). The filtrate was then passed over a DEAE column, immediately applied to an equilibrated heparin column, and eluted along a sodium chloride gradient. Polymerase fractions were collected and dialyzed into Buffer A. Enzymes were further purified using an SP column and again eluted along a salt gradient. Pooled fractions were then applied to a SEPHADEX® 16/60 size exclusion column (GE Healthcare), concentrated, and dialyzed into storage buffer (50 mM Tris-HCl, 50 mM KCl, 0.1 mM EDTA, 1 mM DTT, 0.1% Non-idet P40, 0.1% Tween20, 50% glycerol, pH 8.0). Working stocks were made at 0.2 mg/mL.

PCR Proofreading Assay—

50 µL PCR reactions were set up with a final concentration of 1× Assay Buffer (60 mM Tris-HCl (pH8.4), 25 mM $(NH_4)_2SO_4$, 10 mM KCl), 200 µM dNTPs, 2 mM $MgSO_4$, 400 nM (PCRTest.F/PCRTest.R) or (PCRTest.DiDe.F/PCRTest.DiDe.R) forward and reverse primers, 20 ng of pTET.KOD plasmid and 0.2 µg polymerase. Reactions were thermal-cycled using the following program: 95° C. —1 min, 25× (95° C.—30 sec, 55° C.—30 sec, 68° C.—2 min 30 sec).

Primer Extension Assay—

10 pmol of 5' fluorescein labeled primer (RT.Probe or RT.Probe.3ddc) were annealed with 50 pmol of template RNA or DNA (RT.RNA.TEMP and RT.DNA.TEMP, respectively) and 0.4 µg of polymerase by heat denaturation at 80° C. for 1 minute and allowing to cool to room temperature. Reactions were initiated by the addition of "start" mix which contained (1× Assay Buffer, 2 mM $MgSO_4$ and 200 dNTPs. Reactions were incubated for 10 minutes at 68° C. until terminated by the addition of EDTA to a final concentration of 25 mM. The labeled primer was removed from the template strand by heating sample at 75° C. for 5 minutes in 1× dye (47.5% formamide, 0.01% SDS) and 1 nmol of unlabeled RT.bigBlocker oligonucleotide (to competitively bind the template strand). Samples were run on a 20% (7 M urea) acrylamide gel.

Reverse Transcriptase Fidelity (SSCS)—

Templates for SSCS were prepared by first strand reverse transcription or primer extension (plasmid DNA template) with barcoded primer. Polymerization reactions were carried out according to manufacturer's recommendations for recombinant MMLV (New England Biolabs). For experimental polymerases, reverse transcription or primer extension was performed in 1× Assay Buffer, 200 nM dNTPs, 1 mM $MgSO_4$, 400 nM barcoded reverse primer (HSP.seqBAR.R or pol2.SeqBar.R), 40 units RNasin Plus, 0.2 µg polymerase, and template (1 µg Human heart total RNA or 1 ng plasmid). Reactions were incubated at 68° C. for 30 minutes (cDNA synthesis) or 2 minutes for DNA primer extension. Single stranded products were PCR amplified using Accuprime Pfx polymerase (ThermoFisher) with next-Seq.R and corresponding indexed forward primer. Samples were submitted for ILLUMINA® MISEQ® PE 2×250 sequencer.

Targeted DNA sequencing reads were aligned and grouped based on unique molecular barcodes tagging individual reverse transcription events using ustacks (v1.35). Using a modified version of the single strand consensus sequence program (SSCS) (Schmitt et al., 2012), only groups containing three or more reads were analyzed. From these reads, a consensus sequence was built if more than sixty-six percent of the bases at each position were in agreement, otherwise the base was called as N and disregarded in the remaining analysis. Consensus reads were then aligned to the reference sequence using BWA-MEM (v0.7.7) (Li, 2013), and single nucleotide variants and indels were identified. The polymerase fidelity was calculated as the sum of indels and erroneous bases as a fraction of the total number of aligned bases.

RTPCR Assay—

50 µL reverse transcription PCR (RTPCR) reactions were set up on ice with the following reaction conditions: 1× Assay Buffer, 1 mM $MgSO_4$, 1 M Betaine (Sigma-Aldrich), 200 µM dNTPs, 400 nM reverse primer, 400 nM forward primer, 40 units RNasin Plus (Promega), 0.2 µg polymerase and 1 µg of Total RNA from Jurkat, Human Spleen or *E. coli* (Ambion). Primer sets used: Po1R2A (PolII.R, PolII.F1/F2/F4), p532 (p532.R, p532.F1/F2/F5), rpoC (rpoC.R, rpoC.F1/F2/F4). Reactions were thermal-cycled according to the following parameters: 68° C.—30 min, 25× (95° C.—30 sec, 68° C. (63° C. for rpoC)—30 sec, 68° C.—30 s/kb).

Single Nucleotide Incorporation Kinetics—

Duplexes (DNA:DNA or DNA:RNA) were assembled by combining equimolar amounts of a DNA 25-mer (5'-CCCTCGCAGCCGTCCAACCAACTCA-3') (SEQ ID NO. 8) and DNA or RNA 36-mer (3'-GGGAGCGTCGGCAG-GTTGGTTGAGTGCCTCTTGTTT-5') (SEQ ID NO. 9) in 10 mM Tris-HCl, 0.1 mM EDTA (pH 8.0). Solutions were heated to 95° C. for 5 min, slowly cooled to 60° C. for 10 min, and then cooled to room temperature for 15 minutes. Reactions (100 µL) consisting of assay buffer, 1 mM $MgSO_4$, and 500 nM duplex were initiated by variable amounts of α-P32-dCTP (0.003-400 µM), which was diluted 1:400 in unlabeled dCTP. Reactions were allowed to proceed 3-14 minutes. 10 µL aliquots were quenched by the addition of EDTA (0.25 M final concentration) in 15-120s intervals. Aliquots (2 µL) were spotted on DE81 filter paper and washed 6 times in 5% $NaH_2PO_4$ (pH 7), 2 times in dd$H_2O$ and finally in 95% EtOH. Dried filter paper was exposed for 24 hrs and imaged on a STORM scanner. Initial rates were obtained by analysis using FiJi (Image J). Kinetic parameters were determined by non-linear regression using SigmaPlot10.

RNA Sequencing and Analysis—

RNA from U87MG glioblastoma cells (ATCC® HTB-14) were harvested using trizol LS following manufacturer's instructions (10296-028, Thermo fisher scientific). Ribosomal RNAs were then removed from the RNA samples using RIBO-ZERO® rRNA removal kit (MRZH11124, Epicentre) and cleaned using RNEASY® MINELUTE® Cleanup Kit (Qiagen). rRNA depleted RNAs were fragmented using NEBNEXT® Magnesium RNA Fragmentation Module (E6150S, NEB) to 200-300 bp size range followed by kinase treatment to prepare for adaptor ligation. ILLUMINA® libraries were prepared using NEBNEXT® Multiplex Small RNA Library Prep kit (E7580, NEB) and size selected to remove adaptor dimers using AMPURE® XP beads. Six ILLUMINA® libraries were prepared from the same pool of RNA using experimental reverse transcriptases and PROTOSCRIPT® II Reverse Transcriptase from the library prep kit. RNASeq libraries were sequenced on ILLUMINA® HISEQ® 2000 sequencer, 2×100 bp by the genome sequencing and analysis facility at the University of Texas at Austin.

The evaluation of RNA-seq quality control metrics was performed via RNA-SeQC (v1.1.8) (DeLuca et al., 2012). For transcript abundance analysis, fpkm values were generated through the cufflinks/cuffnorm pipeline (v2.2.1) (Trapnell et al., 2012) and transformed both by log 2 and to fit the range [−3,3].

RNA Sanger Sequencing—

Sanger sequencing reactions were set up by preparing 1× Assay Buffer, 1 mM $MgSO_4$, 10 pmol RT.Probe, 50 pmol SangerGATC Template, 0.4 ug Core3exo-, and 50 µM dNTPs. For the indicated terminator nucleotide, a 25:1 ratio of 3'dideoxy terminator to unmodified NTP was used. Reactions were thermal cycled 6× (68° C. —20 sec, 85° C.—5 sec). Reactions were terminated by the addition of EDTA to a final concentration of 25 mM. The labeled primer was removed by heating sample at 75° C. for 5 minutes in 1× dye (47.5% formamide, 0.01% SDS) and 1 nmol of unlabeled SangerBlocker oligonucleotide.

Example 4

Sequencing of Pairs VH and VL Sequences from B Cells

Isolation of Total B Cells—

Frozen PBMCs (10 million cells in 1 mL) were thawed at 37° C., resuspended in 50 mL of RPMI 1640 (Lonza) supplemented with 10% Fetal Bovine Serum, 1× non-essential amino acids, 1× sodium pyruvate, 1× glutamine, 1× penicillin/streptomycin, and 20 U/mL DNAse I, and recovered via centrifugation (300 g for 10 min at 20° C.). The cells were then resuspended in 4 mL of RPMI and allowed to recover at 37° C. for 30 min. The cells were diluted with 10 mL of cold MACS buffer (PBS supplemented with 0.5% BSA and 2 mM EDTA), collected by centrifugation (300 g for 10 min at 4° C.), and depleted of non-B cells using the Human Memory B Cell Isolation Kit with an LD column (Miltenyi Biotec) as per the manufacturer's instructions. This yielded 400,000-500,000 B cells per vial.

Amplification of the Paired VH:VL Repertoire—

The paired VH and VL sequences were determined using a custom designed axisymmetric flow focusing device (DeKosky et al., 2016) that is comprised of three concentric tubes. Total B cells were suspended in 6 mL of cold PBS and passed through the innermost tube at a rate of 0.5 mL/min. Oligo d(T)$_{25}$ magnetic beads (1 µm diameter at a concentration of 45 µL beads/mL solution; NEB) were washed, subjected to focused ultrasonication (Covaris) to dissociate any aggregates, resuspended in 6 mL of lysis buffer (100 mM Tris-HCl pH 7.5, 500 mM LiCl, 10 mM EDTA, 1% Lithium dodecyl sulfate (LiDS), 5 mM DTT), and passed through the middle tube at a rate of 0.5 mL/min. The outer tubing contained an oil phase (mineral oil containing 4.5% Span-80, 0.4% Tween-80, and 0.05% Triton X-100; Sigma-Aldrich) flowing at 3 mL/min. The cells, beads, and lysis buffer were emulsified as they passed through a custom designed 120 μm diameter orifice, and were subsequently collected in 2 mL microcentrifuge tubes. Each tube was inverted several times, incubated at 20° C. for 3 minutes, and then placed on ice. Following the collection phase, emulsions were pooled into 50 mL conicals, and centrifuged (4,000 g for 5 min at 4° C.). The mineral oil (upper phase) was decanted, and the emulsions (bottom phase) were broken with water-saturated cold diethyl ether (Fischer). Magnetic beads were recovered following a second centrifugation step (4,000 g for 5 min at 4° C.) and resuspended in 1 mL of cold Buffer 1 (100 mM Tris pH 7.5, 500 mM LiCl, 10 mM EDTA, 1% LiDS, 5 mM DTT). The beads were then serially pelleted using a magnetic rack, and washed with the following buffers: 1 mL lysis buffer, 1 mL Buffer 1, and 0.5 mL Buffer 2 (20 mM Tris pH 7.5, 50 mM KCl, 3 mM MgCl). The beads were split into two aliquots, and each was then pelleted one final time and resuspended in an RT-PCR mixture (DeKosky et al., 2016) containing VH and VL Framework Region 1 (FR1) linkage primers or VH and VL leader peptide (LP) linkage primers and either the CORE3 enzyme "RTX" or a conventional reverse transcriptase "Quanta". The RT-PCR mixtures were then added dropwise to 9 mL of chilled oil phase in an IKA dispersing tube (DT-20, VWR) and emulsified using an emulsion dispersing apparatus (ULTRA-TURRAX® Tube Drive; IKA) for 5 min. The emulsions were aliquoted into 96-well PCR plates (100 uL/well), and subjected to RT-PCR under the following conditions: 30 min at 55° C. followed by 2 min at 94° C.; 4 cycles of 94° C. for 30 s, 50° C. for 30 s, 72° C. for 2 min; 4 cycles of 94° C. for 30 s, 55° C. for 30 s, 72° C. for 2 min; 32 cycles of 94° C. for 30 s, 60° C. for 30 s, 72° C. for 2 min; 72° C. for 7 min; held at 4° C.

Following RT-PCR, the emulsions were collected in 2 mL microcentrifuge tubes and centrifuged (16000 g for 10 min at 20° C.). The mineral oil (upper phase) was decanted, and water-saturated ether was used to break the emulsions. The aqueous phase (containing the DNA) was extracted three times by sequentially adding ether, centrifuging the samples (16000 g for 30 s at 20° C.), and removing the upper ether phase. Trace amounts of ether were removed using a Speed-Vac for 30 min at 20° C. The DNA amplicons were purified using a silica spin column (Zymo Research) according to the manufacturer's instructions, and eluted in 40 μL H$_2$O. The two samples were then amplified through a nested PCR using Platinum Taq (Life Technologies) under the following conditions: (FR1 primer derived sample) 2 min at 94° C., 32 cycles of 94° C. for 30 s, 62° C. for 30 s, 72° C. for 20 s; 72° C. for 7 min; held at 4° C.; (LP primer derived sample) 2 min at 94° C., 27 cycles of 94° C. for 30 s, 62° C. for 30 s, 72° C. for 20 s; 72° C. for 7 min; held at 4° C. The amplicons, approximately 850 bp in length, were gel purified from 1% agarose using a gel extraction kit (Zymo Research) according to the manufacturer's instructions, and eluted in 20 μL H$_2$O.

Figure 13:
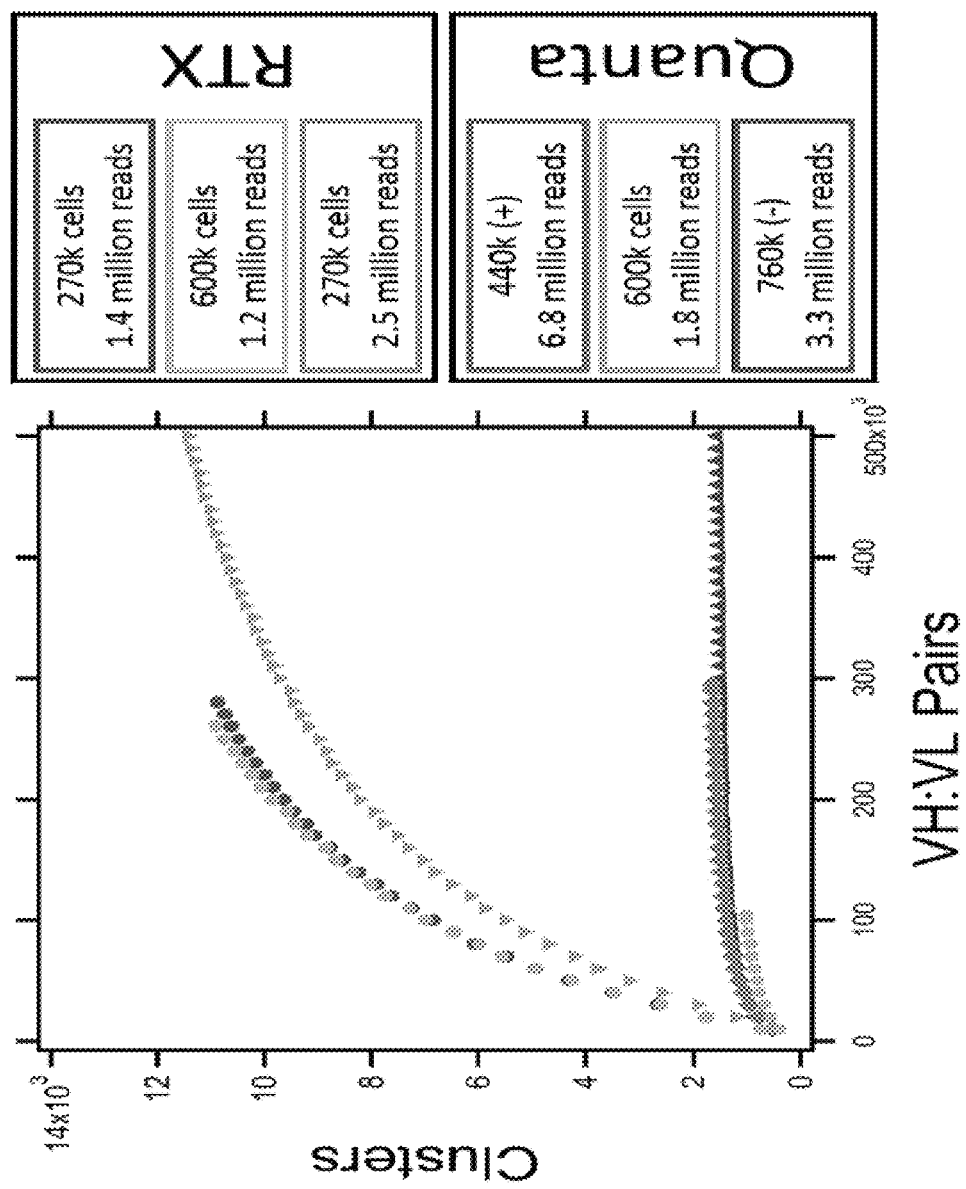
FIG. 13. The table shows the results of paired VH:VL coding sequence amplification using the CORE3 enzyme ("RTX") versus a conventional reverse transcriptase ("Quanta").

To determine the full length VH and VL reads for antibody expression studies, the paired amplicon was subjected to an additional PCR using NEBNEXT® high fidelity polymerase (NEB) to specifically amplify the full VH chain and the full VL chain separately in addition to the paired chains (Note: the paired reads sequence the entire J- and D-regions, and the fragment of the V regions spanning FR2 to CDR3). Each sample was split into 5 reactions and subjected to the following PCR conditions: 30 sat 98° C., X cycles of 98° C. for 10 s, 62° C. for 30 s, 72° C. for Y s; 72° C. for 7 min; held at 4° C. Finally, these sequences were amplified one final time with TSBC compatible barcoding primers following the protocol shown in, gel purified from 1% agarose using a gel purification kit according to manufacturer's instructions, and submitted for paired-end ILLUMINA® next-generation sequencing. The clustering of the resulting VH:VL pairs obtained by using the CORE3 enzyme versus a conventional RT are shown in FIG. 13.

Example 5

Reverse Trascriptase and 2' 0-Methyl DNA Activity

Primer Extension Assay—

5 pmol of 5' fluorescein labeled primer (RT.NoU.Probe) were annealed with 12.5 pmol of template RNA (RT.NoU.Template) and 0.4 μg of polymerase by heat denaturation at 80° C. for 1 minute and allowing to cool to room temperature. For these studies the template RNA was designed to lack "U" positions. Reactions were initiated by the addition of "start" mix which contained: 1× Assay Buffer, 1 mM MgSO$_4$ and 200 μM dNTPs. Reactions were incubated for 30 minutes at 68° C. The labeled primer was removed from the template strand by heating sample at 75° C. for 5 minutes in 1× dye (47.5% formamide, 0.01% SDS) and 1 nmol of unlabeled blocker oligonucleotide (to competitively bind the template strand). Samples were run on a 15% (7 M urea) acrylamide gel.

DNA Sequences

```
RT.NoU.Tern plate
                                      (SEQ ID NO: 10)
ACGCAAGGAGGCAAACGGAAAACAACGAGCAGGAGGGACGGCAGCG

AGGG

RT.NoU.Probe
                                      (SEQ ID NO: 11)
CCCTCGCTGCCGTCCCTCCTG
```

Figure 14:
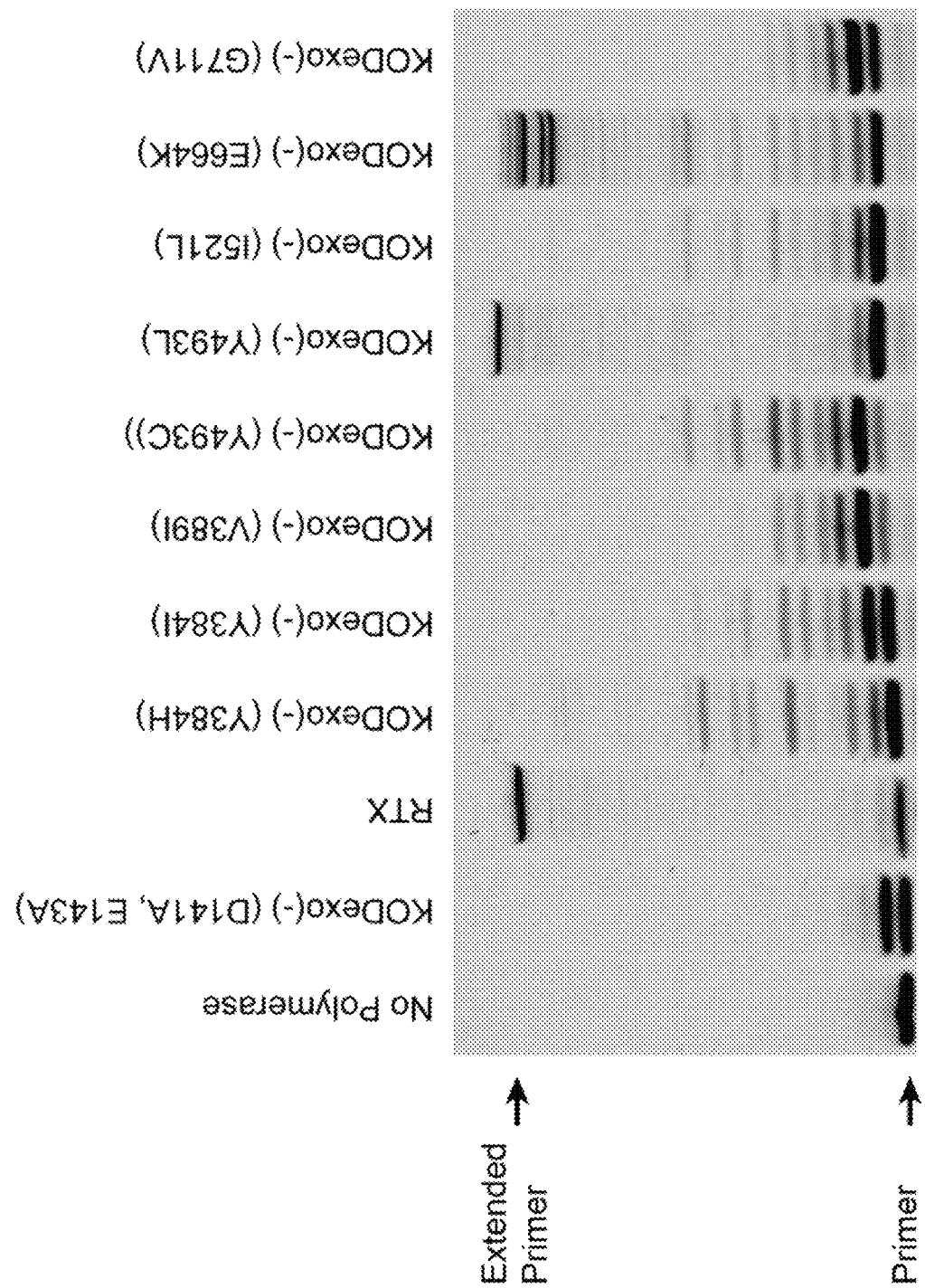
FIG. 14. Individual amino acid substitutions we tested for ability to provide primer extension activity using an RNA template. A base KOD enzyme, lacking exonuclease activity (by introduction of the D141A and E143A substitutions), was used as the negative control and background for testing the effect of individual substitutions of RNA-templated primer extension activity. The CORE3 enzyme ("RTX") is shown as the positive control. Results of the study show that each of the tested substitutions showed enhanced primer extension (RT) activity on a RNA template as compared to the negative control. The Y493L substitution showing the most robust activity for a single substitution.

Polymerase enzymes tested in the studies were based on the KOD enzyme, lacking exonuclease activity (by introduction of the D141A and E143A substitutions). This enzyme served as both the negative control and background for testing the effect of individual substitutions of RNA-templated primer extension activity. The CORE3 enzyme ("RTX") was used as the positive control. The individual substitutions tested where Y384H, Y384I, V389I, Y493C, Y493L, I521L, E664K and G711V. Results of the studies in FIG. 14 show that each of the tested substitutions showed enhanced primer extension (RT) activity on a RNA template as compared to the negative control, with the Y493L substitution showing the most robust activity.

Figure 15:
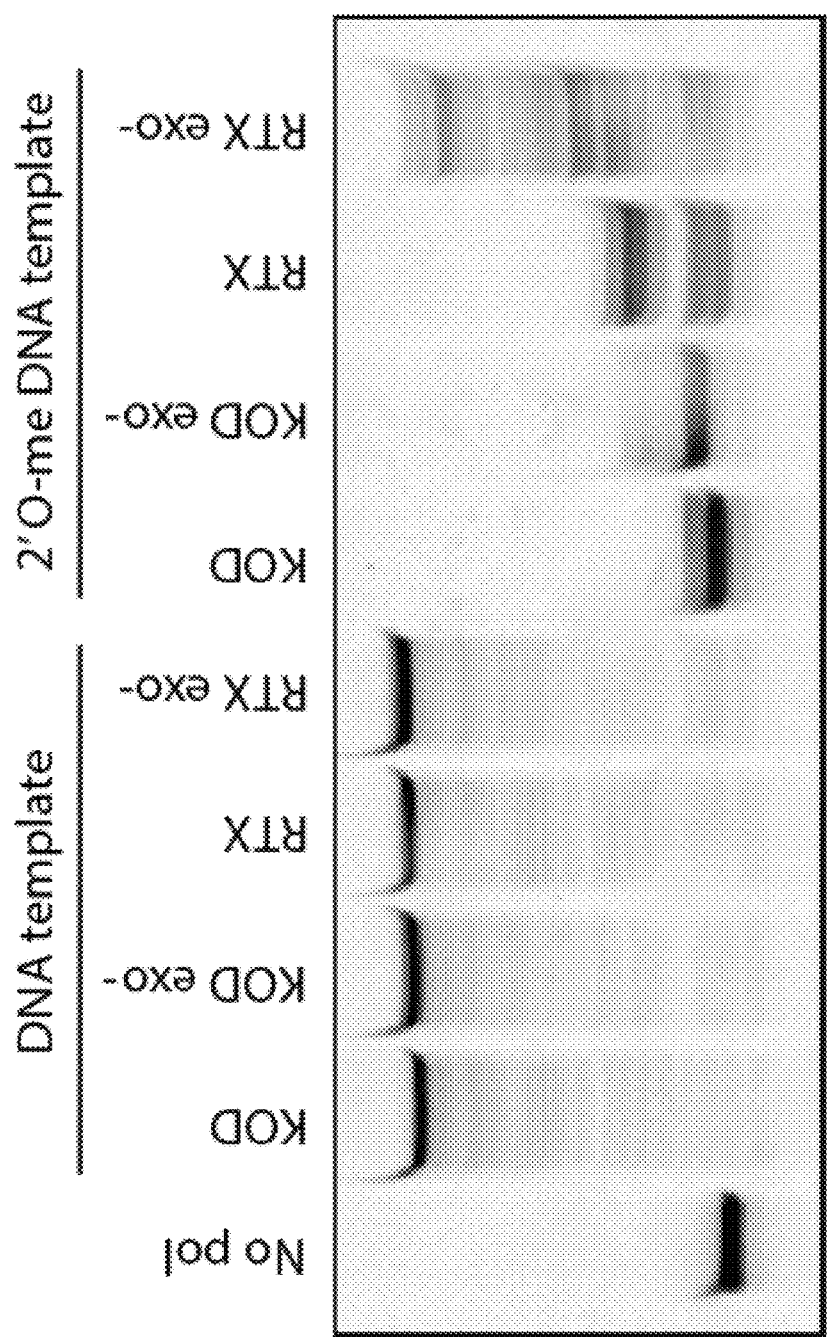
FIG. 15. Primer extension reactions on DNA and 2' O-methyl DNA templates using KOD, KOD exo-, CORE3 ("RTX") and CORE3 exo- ("RTX exo-"). KOD polymerases were not capable of primer extension on 2' O-methyl DNA templates. RTX enzymes could polymerize across 2' O-methyl templates, however full length extension products were only obtained with the proofreading deficient RTX.

Polymerase enzymes were also tested for ability to polymerize from a 2' O-methyl DNA template. Primer extension reactions were performed on a ribose sugar analog [2' O-methyl (Me) DNA] that indicated that CORE3 ("RTX") reverse transcription activity could extend alternative templates, although with lower efficiency, indicating a preference for RNA substrates (FIG. 15). However, the CORE3 enzyme "RTX" was still far more efficient at using 2'-OMeDNA than the parental wild-type.

Although the present disclosure and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS AND PATENT APPLICATIONS

EP 1317539B

PUBLICATIONS

Aird, D. et al. Analyzing and minimizing PCR amplification bias in ILLUMINA® sequencing libraries. *Genome Biol.* 12, R18 (2011).

Baltimore, D. RNA-dependent DNA polymerase in virions of RNA tumour viruses. *Nature* 226, 1209-1211 (1970).

Bergen, K., Betz, K., Welte, W., Diederichs, K. & Marx, A. Structures of KOD and 9° N DNA Polymerases Complexed with Primer Template Duplex. *ChemBioChem* 14, 1058-1062 (2013).

Boeke, J. D. & Stoye, J. P. in Retroviruses (eds. Coffin, J. M., Hughes, S. H. & Varmus, H. E.) (Cold Spring Harbor Laboratory Press, 1997). at available on the world wide web at ncbi.nlm.nih.gov/books/NBK19468/>

Cozens, C., Pinheiro, V. B., Vaisman, A., Woodgate, R. & Holliger, P. A short adaptive path from DNA to RNA polymerases. *Proc. Natl. Acad. Sci.* 109, 8067-8072 (2012).

DeKosky et al., Large-scale sequence and structural comparisons of human naive and antigen-experienced antibody repertoires. *Proc. Nat. Acad. Sci.* (2016).

DeLuca, D. S. et al. RNA-SeQC: RNA-seq metrics for quality control and process optimization. *Bioinforma. Oxf. Engl.* 28, 1530-1532 (2012).

Eigen, M. Selforganization of matter and the evolution of biological macromolecules. *Naturwissenschaften* 58, 465-523 (1971).

Firbank, S. J., Wardle, J., Heslop, P., Lewis, R. J. & Connolly, B. A. Uracil Recognition in Archaeal DNA Polymerases Captured by X-ray Crystallography. *J. Mol. Biol.* 381, 529-539 (2008).

Fogg, M. J., Pearl, L. H. & Connolly, B. A. Structural basis for uracil recognition by archaeal family B DNA polymerases. *Nat. Struct. Biol.* 9, 922-927 (2002).

Ghadessy, F. J., Ong, J. L. & Holliger, P. Directed evolution of polymerase function by compartmentalized self-replication. *Proc. Natl. Acad. Sci.* 98, 4552-4557 (2001).

Greagg, M. A. et al. A read-ahead function in archaeal DNA polymerases detects promutagenic template-strand uracil. *Proc. Natl. Acad. Sci. U S. A.* 96, 9045-9050 (1999).

Hansen, K. D., Brenner, S. E. & Dudoit, S. Biases in ILLUMINA® transcriptome sequencing caused by random hexamer priming. *Nucleic Acids Res.* 38, e131-e131 (2010).

Killelea, T. et al. Probing the Interaction of Archaeal DNA Polymerases with Deaminated Bases Using X-ray Crystallography and Non-Hydrogen Bonding Isosteric Base Analogues. *Biochemistry (Mosc.)* 49, 5772-5781 (2010).

Kim, T. W., Delaney, J. C., Essigmann, J. M. & Kool, E. T. Probing the active site tightness of DNA polymerase in subangstrom increments. *Proc. Natl. Acad. Sci. U S. A.* 102, 15803-15808 (2005).

Klarmann, G. J., Schauber, C. A. & Preston, B. D. Template-directed pausing of DNA synthesis by HIV-1 reverse transcriptase during polymerization of HIV-1 sequences in vitro. *J. Biol. Chem.* 268, 9793-9802 (1993).

Lauring, A. S. & Andino, R. Quasispecies Theory and the Behavior of RNA Viruses. *PLoS Pathog.* 6, e1001005 (2010).

Li, H. Aligning sequence reads, clone sequences and assembly contigs with BWA-MEM; alignment algorithm online at the arXiv website of Cornell University Library. (2013).

Lundberg, K. S. et al. High-fidelity amplification using a thermostable DNA polymerase isolated from *Pyrococcus furiosus*. *Gene* 108, 1-6 (1991).

Nishioka, M. et al. Long and accurate PCR with a mixture of KOD DNA polymerase and its exonuclease deficient mutant enzyme. *J. Biotechnol.* 88, 141-149 (2001).

Pinheiro, V. B. et al. Synthetic Genetic Polymers Capable of Heredity and Evolution. *Science* 336, 341-344 (2012).

Roberts, J. D., Bebenek, K. & Kunkel, T. A. The accuracy of reverse transcriptase from HIV-1. *Science* 242, 1171-1173 (1988).

Schmitt, M. W. et al. Detection of ultra-rare mutations by next-generation sequencing. *Proc. Natl. Acad. Sci.* 109, 14508-14513 (2012).

Takagi, M. et al. Characterization of DNA polymerase from *Pyrococcus* sp. strain KOD1 and its application to PCR. *Appl. Environ. Microbiol.* 63, 4504-4510 (1997).

Temin, H. M. & Mizutani, S. RNA-dependent DNA polymerase in virions of Rous sarcoma virus. *Nature* 226, 1211-1213 (1970).

Trapnell, C. et al. Differential gene and transcript expression analysis of RNA-seq experiments with TopHat and Cufflinks. *Nat. Protoc.* 7, 562-578 (2012).

Wang, A. H.-J. et al. Molecular structure of r(GCG)d (TATACGC): a DNA-RNA hybrid helix joined to double helical DNA. *Nature* 299, 601-604 (1982).

Wei, X. et al. Viral dynamics in human immunodeficiency virus type 1 infection. *Nature* 373, 117-122 (1995).

Xiong, Y. & Eickbush, T. H. Origin and evolution of retroelements based upon their reverse transcriptase sequences. *EMBO J.* 9, 3353-3362 (1990).

What is claimed is:

1. A recombinant Archaeal Family-B polymerase comprising an amino acid sequence at least 95% identical to SEQ ID NO: 1 and comprising an amino acid substitution corresponding to position Y493 to a leucine residue or a cysteine residue.

2. The polymerase of claim 1, further comprising an amino acid substitution at a position corresponding to position E664 in the amino acid sequence shown in SEQ ID NO:1.

3. The polymerase of claim 1, in which one or more amino acid residues at a position corresponding to positions Y384, V389, I521 and G711 in the amino acid sequence shown in SEQ ID NO:1 is substituted with another amino acid residue.

4. The polymerase of claim 1, comprising an amino acid substitution corresponding to position Y493 to a leucine residue.

5. The polymerase of claim 3, comprising an amino acid substitution corresponding to position Y384 to a phenylalanine residue, a leucine residue, an alanine residue, a cysteine residue, a serine residue, a histidine residue, an isoleucine residue, a methionine residue, an asparagine residue, or a glutamine residue.

6. The polymerase of claim 5, comprising an amino acid substitution corresponding to position Y384 to a histidine residue or an isoleucine residue.

7. The polymerase of claim 3, comprising an amino acid substitution corresponding to position V389 to a methionine residue, a phenylalanine residue, a threonine residue, a tyrosine residue, a glutamine residue, an asparagine residue, or a histidine residue.

8. The polymerase of claim 7, comprising an amino acid substitution corresponding to position V389 to an isoleucine residue.

9. The polymerase of claim 3, comprising an amino acid substitution corresponding to position I521 to a leucine.

10. The polymerase of claim 2, comprising an amino acid substitution corresponding to position E664 to a lysine residue.

11. The polymerase of claim 3, comprising an amino acid substitution corresponding to position G711 to a leucine residue, a cysteine residue, a threonine residue, an arginine residue, a histidine residue, a glutamine residue, a lysine residue, or a methionine residue.

12. The polymerase of claim 11, comprising an amino acid substitution corresponding to position G711 to a valine residue.

13. The polymerase of claim 1, comprising an amino acid substitution corresponding to position R97 to an another amino acid residue.

14. The polymerase of claim 1, comprising an amino acid substitution corresponding to one or more of the positions selected from the group consisting of positions A490, F587, M137, K118, T514, R381, F38, K466, E734 and N735 with another amino acid residue.

15. The polymerase of claim 1, wherein the polymerase has proofreading activity.

16. The polymerase of claim 1, wherein the polymerase lacks proofreading activity.

17. The polymerase of claim 1, wherein the polymerase transcribes a template that is RNA.

18. The polymerase of claim 1, wherein the polymerase transcribes at least 10 nucleotides from a RNA template.

19. The polymerase of claim 1, wherein the polymerase has thermophilic activity.

20. The polymerase of claim 1, wherein the polymerase transcribes a template that is 2'-OMethyl DNA.

* * * * *